US011833233B2

(12) United States Patent
Vanderhoof et al.

(10) Patent No.: US 11,833,233 B2
(45) Date of Patent: Dec. 5, 2023

(54) ALKALI-SWELLABLE MULTI-FUNCTIONAL RHEOLOGY MODIFIERS

(71) Applicant: NOURYON CHEMICALS INTERNATIONAL B.V., Arnhem (NL)

(72) Inventors: Matthew Michael Vanderhoof, Hixson, TN (US); Klin Aloysius Rodrigues, Signal Mountain, TN (US); Sajal Pantha, Ooltewah, TN (US); Andrew James Bailey, Chattanooga, TN (US)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 320 days.

(21) Appl. No.: 16/764,523

(22) PCT Filed: Nov. 16, 2018

(86) PCT No.: PCT/EP2018/081522
§ 371 (c)(1),
(2) Date: May 15, 2020

(87) PCT Pub. No.: WO2019/096976
PCT Pub. Date: May 23, 2019

(65) Prior Publication Data
US 2021/0371567 A1    Dec. 2, 2021

Related U.S. Application Data

(60) Provisional application No. 62/588,041, filed on Nov. 17, 2017.

(30) Foreign Application Priority Data

Mar. 8, 2017    (EP) ..................... 18160646

(51) Int. Cl.
| | | |
|---|---|---|
| *A01N 25/28* | (2006.01) | |
| *A61K 8/02* | (2006.01) | |
| *A61Q 19/00* | (2006.01) | |
| *C08F 265/06* | (2006.01) | |
| *A61K 8/81* | (2006.01) | |
| *A61Q 5/06* | (2006.01) | |
| *C08F 220/18* | (2006.01) | |
| *A61K 8/06* | (2006.01) | |
| *C08F 220/06* | (2006.01) | |
| *C08F 220/14* | (2006.01) | |

(52) U.S. Cl.
CPC .......... *A61K 8/0283* (2013.01); *A61K 8/8147* (2013.01); *A61Q 5/06* (2013.01); *C08F 265/06* (2013.01); *A61K 8/022* (2013.01); *A61K 8/06* (2013.01); *A61K 2800/654* (2013.01); *C08F 220/06* (2013.01); *C08F 220/14* (2013.01); *C08F 220/1802* (2020.02)

(58) Field of Classification Search
CPC .... C08F 261/00; C08F 265/00; C08F 265/02; C08F 265/06; C08F 265/04; C08F 220/1802; C08F 220/06; C08F 220/14
See application file for complete search history.

(56) References Cited

U.S. PATENT DOCUMENTS

| | | | |
|---|---|---|---|
| 3,929,678 | A | 12/1975 | Laughlin et al. |
| 4,529,773 | A | 7/1985 | Witiak et al. |
| 4,565,647 | A | 1/1986 | Llenado |
| 5,571,552 | A | 11/1996 | Kasica et al. |
| 5,720,964 | A | 2/1998 | Murray |
| 5,858,948 | A | 1/1999 | Ghosh et al. |
| 6,462,013 | B1 | 10/2002 | Cooke, Jr. et al. |
| 6,573,375 | B2 | 6/2003 | Polovsky et al. |
| 6,635,702 | B1 | 10/2003 | Schmucker-Castner et al. |
| 6,727,357 | B2 | 4/2004 | Polovsky et al. |
| 6,897,253 | B2 | 5/2005 | Schmucke-Castner et al. |
| 8,673,277 | B2 | 3/2014 | Tamareselvy et al. |
| 2004/0127603 | A1 | 7/2004 | Lean et al. |
| 2006/0002875 | A1 | 1/2006 | Winkler et al. |
| 2013/0183361 | A1 | 7/2013 | Tamareselvy et al. |
| 2020/0255568 | A1* | 8/2020 | Hsu .......... C08F 2/001 |

FOREIGN PATENT DOCUMENTS

| | | |
|---|---|---|
| WO | 99/21530 A1 | 5/1999 |
| WO | 2006/119960 A1 | 11/2006 |
| WO | 2015/164059 A1 | 10/2015 |

* cited by examiner

*Primary Examiner* — Irina S Zemel
*Assistant Examiner* — Jeffrey S Lenihan
(74) *Attorney, Agent, or Firm* — Norris McLaughlin, P.A.

(57) ABSTRACT

Alkali-swellable rheology modifier comprising a core-shell polymer comprising a core polymer and a shell comprising at least one shell copolymer layer at least partially cross-linked and containing a mole percent of crosslinking agent greater than the mole percent of crosslinking agent in the core polymer, provided if the mole percent of crosslinking agent in the core polymer is zero, then either the core polymer is greater than 60 wt % of the core-shell polymer; the core polymer comprises at least one associative monomer; at least one shell copolymer layer copolymer comprises at least one associative monomer; and/or the at least one shell copolymer layer that is at least partially cross-linked comprises greater than 3 mole % crosslinking agent. Aqueous compositions comprising the alkali-swellable rheology modifier include personal care formulations, healthcare formulations, agricultural formulations, paint formulations, coating formulations, laundry and fabric care formulations, household cleaning formulations, and industrial and institutional cleaning formulations.

18 Claims, 2 Drawing Sheets

ALKALI-SWELLABLE MULTI-FUNCTIONAL RHEOLOGY MODIFIERS

This application is a 371 of PCT/EP2018/081522, filed Nov. 16, 2018, which claims priority of U.S. Provisional Application No. 62/588,041, filed Nov. 17, 2017, and foreign priority benefit under 35 U.S.C. § 119 of European Patent Application No. 18160646.8, filed Mar. 8, 2018, the disclosures of which patent applications are incorporated herein by reference.

FIELD OF THE DISCLOSURE

In one aspect, the present application relates to rheology modifiers comprising alkali-swellable core-shell polymers comprising a core and at least one crosslinked shell layer, wherein the mole percent of crosslinking agent in the at least one crosslinked shell layer is greater than the mole percent of crosslinking agent in the core. In another aspect, the application relates such to alkali-swellable core-shell polymer rheology modifiers suitable for use in aqueous systems, and which rheology modifiers provide other functions useful in a finished formulation. Additionally, the application relates to the formation of rheologically and phase stable aqueous surfactant compositions comprising such alkali-swellable core-shell polymers.

BACKGROUND OF THE DISCLOSURE

Rheology modifiers, also referred to as thickeners or viscosifiers, are ubiquitous in various commercial formulations, such as personal care formulations, healthcare formulations, agricultural formulations, paint formulations, coating formulations, laundry and fabric care formulations, household cleaning formulations, and industrial and institutional cleaning formulations. Rheological modifiers can be selected for a particular formulation to provide rheological properties for a particular purpose. For example, for personal care formulations, the rheological modifier can be selected for its ability to provide viscosity and flow characteristics, foamability, spreadability, clarity, sensory effects, and mildness.

Carbomers are one type of thickener known in the art of personal care formulations. Carbomers, which are synthetic polymers based on acrylic acid monomers, are typically supplied as powders.

In personal care hair styling compositions, thickeners such as carbomers are typically used in combination with another polymer that forms a film on hair to serve as a hair fixative. Carbomers are generally incompatible with ionic polymers, therefore the other fixative polymers used in combination with carbomers are typically nonionic. One such nonionic fixative polymer commonly used with carbomers is polyvinylpyrrolidone. Although other fixative polymers, particularly anionic polymers, are known to be more effective hair fixatives than polyvinylpyrrolidone, these other fixative polymers have limited compatibility with carbomers. Thus the use of carbomer rheology modifiers can impose significant limitations on personal care formulators in the choice of other hair fixative polymers and other ingredients that can go into a personal care formulation.

Carbomer powders also can be difficult to incorporate into a personal care formulation. During processing, carbomer powders can become electrostatically charged as they are transferred in and out of containers and tend to adhere to oppositely charged surfaces including airborne dust, necessitating specialized dust extraction equipment. The powdered material can also agglomerate during the rehydration process, leading to "fish-eyes" which are difficult to completely disperse and can persist into the finished product. This means that preparation of aqueous dispersions is messy, energy-intensive and time-consuming unless special precautions and expensive equipment is employed. Formulators of compositions containing thickened surfactant constituents desire the ability to formulate their products at ambient temperatures (cold processing). Thus for some formulations it would be desirable to provide rheology modifier compositions in either a liquid form, or a powder form that is more readily dispersible and less prone to dusting than carbomer powders.

To avoid these problems of the prior art, it would be desirable to have a rheology modifier that is easy to use, provides desirable rheology characteristics, and has good solubility. For some formulations, it also would be desirable to have a rheology modifier that provides good clarity. It further would be desirable to have a rheology modifier that provides these qualities, and further provides hair fixative functionality, to reduce or eliminate the need for an additional fixative component in a hair fixative personal care composition in which the rheology modifier is present. It further would be desirable for such a rheology modifier to provide these qualities over a range of pH values of at least about 4.5-9. Still further, it would be desirable if at least a portion of the rheology was derived from a natural, renewable resource.

SUMMARY OF THE DISCLOSURE

In one aspect, the application relates to alkali-swellable rheology modifiers suitable for use in aqueous compositions, the alkali swellable rheology modifiers comprising at least one core-shell polymer, the core-shell polymer comprising a core polymer and a shell comprising at least one shell copolymer layer, wherein the at least one shell copolymer layer is an at least partially cross-linked copolymer containing a mole percent of crosslinking agent greater than the mole percent of crosslinking agent in the core polymer, with the proviso that if the mole percent of crosslinking agent in the core polymer is zero, then the core-shell polymer is characterized by at least one of the following (a) the core polymer is greater than 60% by weight of the core-shell polymer; (b) the core polymer comprises at least one associative monomer; (c) at least one shell copolymer layer comprises at least one associative monomer; or (d) the monomers of the at least one shell copolymer layer that is at least partially cross-linked comprise greater than 3 mol % crosslinking agent, based on the moles of monomers in that shell copolymer layer not counting the crosslinking agent.

The application further relates to aqueous compositions comprising such alkali swelling rheology modifiers.

In one aspect, the weight proportion of shell to core and the amount of crosslinking agent in each of the shell and the core are selected to provide preferred rheological properties for a particular end-use application.

The core polymer and the at least one shell copolymer layer are each polymerized from a monomer composition comprising a) one or more anionic ethylenically unsaturated monomers; b) one or more hydrophobic ethylenically unsaturated monomers; c) optionally one or more nonionic ethylenically unsaturated monomers; and d) optionally one or more associative monomers. At least one of the shell copolymer layers will also include one or more crosslinking agents. The core polymer optionally can include one or more crosslinking agents.

In one aspect, the alkali-swellable rheology modifier comprises a core-shell polymer wherein the core polymer contains zero mol % crosslinking agent, and the core polymer is greater than 60 wt % of the core-shell polymer.

In one aspect, the alkali-swellable rheology modifier comprises a core-shell polymer wherein the core polymer contains zero mol % crosslinking agent, and the core polymer comprises an associative monomer.

In one aspect, the alkali-swellable rheology modifier comprises a core-shell polymer wherein the core polymer contains zero mol % crosslinking agent, and at least one shell copolymer layer comprises an associative monomer.

In one aspect, the alkali-swellable rheology modifier comprises a core-shell polymer wherein the core polymer contains zero mol % crosslinking agent, and at least one shell copolymer layer comprises greater than 3 mol % crosslinking agent, based on the moles of monomers in that shell copolymer layer not counting the crosslinking agent.

In one aspect, the alkali-swellable rheology modifier comprises a core-shell polymer wherein the core polymer contains at least 0.01 mol % crosslinking agent.

In one aspect, the alkali-swellable rheology modifier comprises a core-shell polymer wherein the core polymer contains at least 0.01 mol % crosslinking agent, and the core is greater than 60 wt % of the core-shell polymer.

In one aspect, the alkali-swellable rheology modifier comprises a core-shell polymer wherein the core polymer contains at least 0.01 mol % crosslinking agent, and the core polymer comprises an associative monomer.

In one aspect, the alkali-swellable rheology modifier comprises a core-shell polymer wherein the core polymer contains at least 0.01 mol % crosslinking agent, and the at least one shell copolymer layer comprises an associative monomer.

In one aspect, the alkali-swellable rheology modifier comprises a core-shell polymer wherein the core contains at least 0.01 mol % crosslinking agent, and at least one shell copolymer layer comprises greater than 3 mol % crosslinking agent, based on the moles of monomers in that shell copolymer layer not counting the crosslinking agent.

In some embodiments, the alkali-swellable rheology modifier comprises a core-shell polymer that includes $C_1$-$C_6$ alkyl (meth)acrylate monomers. In some embodiments, the core-shell polymers include both at least one $C_1$-$C_6$ alkyl acrylate monomer and at least one $C_1$-$C_6$ alkyl methacrylate monomer.

In another aspect, the application relates to alkali-swellable rheology modifiers comprising core-shell polymers and further comprising a spray-drying adjuvant.

In another aspect, the application relates to alkali-swellable rheology modifiers comprising core-shell polymers and further comprising a spray-drying adjuvant derived from a natural, renewable resource.

In one embodiment, the natural renewable resource from which the spray-drying adjuvant is derived is a polysaccharide.

In one embodiment, the natural renewable resource from which the spray-drying adjuvant is derived is based on cellulose.

In one embodiment, the natural renewable resource from which the spray-drying adjuvant is derived is based on starch.

In another aspect, the application relates to alkali-swellable rheology modifiers comprising core-shell polymers and further comprising a spray-drying adjuvant derived from a polyvinyl acetate derivative.

In one embodiment, a method of making an alkali-swellable rheology modifier composition comprises the steps of (i) providing an alkali-swellable core-shell polymer as disclosed herein, (ii) blending the core-shell polymer with a spray-drying adjuvant, and (iii) drying the blend; whereby the alkali-swellable rheology modifier is in the form of a dried powder.

In another aspect the application relates to aqueous polymer emulsions comprising an alkali-swellable core-shell polymer as described herein.

In another aspect, the application relates to formulations comprising alkali-swellable rheology modifiers as disclosed herein.

In one embodiment, the formulations comprising alkali-swellable rheology modifiers as disclosed herein are selected from personal care formulations, healthcare formulations, agricultural formulations, paint formulations, coating formulations, laundry and fabric care formulations, household cleaning formulations, and industrial and institutional cleaning formulations, and formulations for use in electronics industries, and formulations for use in construction industries.

In one embodiment, the formulations are aqueous formulations further comprising one or more surfactants. The surfactants can be selected from any of anionic, cationic, amphoteric and nonionic surfactants, and mixtures thereof.

In one embodiment, the formulations are personal care formulations.

In one embodiment, the personal care formulations are hair fixative formulations, and the alkali-swellable rheology modifiers provide the additional function of film-forming, such that the rheology modifier also functions as a hair fixative ingredient in the formulation.

DETAILED DESCRIPTION

Figure 1:
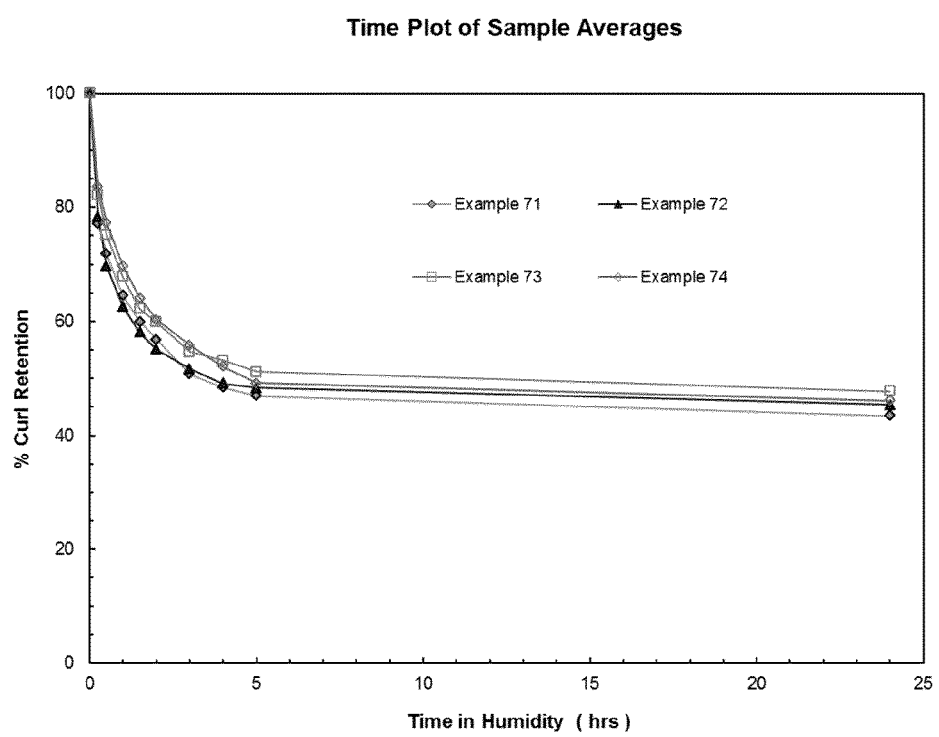
FIG. 1 is a graph of percent curl retention over time in a high humidity curl retention evaluation of hair gel formulations of Examples 71-74, evaluated as described in Example 82.

Exemplary embodiments in accordance with the present application will be described. Various modifications, adaptations or variations of the exemplary embodiments described herein may become apparent to those skilled in the art as such are disclosed. It will be understood that all such modifications, adaptations or variations that rely upon the teachings of the present application, and through which these teachings have advanced the art, are considered to be within the scope and spirit hereof.

The polymers and compositions disclosed herein may suitably comprise, consist of, or consist essentially of the components, elements, and process delineations described herein. The embodiments illustratively disclosed herein suitably may be practiced in the absence of any element which is not specifically disclosed herein.

In the context of the disclosure the term "(co)polymer" indicates polymer or copolymer. The term "polymer" and the term "copolymer" are used herein interchangeably.

As used herein and throughout the specification, the terms "core-shell morphology", "core-shell structure", "core-shell polymer", "staged core-shell polymer" and "two-staged polymer" or "multi-staged polymer" are used interchangeably and mean a polymer particle prepared by a sequential or staged polymerization process wherein each sequence or stage of monomer repeating units is added to the polymerization reactor and begins to undergo polymerization before the addition and polymerization of the subsequent sequence or stage of repeating units is commenced. In some embodiments the polymerization of one stage will be substantially complete before the monomers of the next stage are added to the polymerization reactor; in some embodiments the polymerization of one stage may be only partially complete before the monomers of the next stage are added to the polymerization reactor. As best understood, these core-shell polymers disclosed herein have a structure in which a polymer(s) forming the core portion, sequence or stage and the polymer(s) forming the shell portion, sequence or stage are physically and/or chemically bonded and/or attracted to each other. The structure and/or chemical composition (e.g., monomer composition and/or amount) of the disclosed copolymer particles changes from the inside to the outside of the particle and, as a result, these gradient zones can have different physical and chemical properties as well. These changes can be somewhat gradual, yielding a morphology having a gradient of polymeric structure or composition along any radius thereof. Alternatively, the change in polymeric structure or composition can be relatively well defined when moving outward along a radius of the particle from the center, yielding a morphology having a relatively distinct core portion comprising one polymeric composition, and a relatively distinct shell portion comprising a different polymeric composition. The staged core-shell morphology can comprise multiple layers or zones of differing polymeric composition as long as at least one shell copolymer layer is an at least partially cross-linked polymer containing a mole percent of crosslinking agent greater than the mole percent of crosslinking agent in the core polymer. The rate of change in the polymeric morphology of the particle is not particularly critical as long as the polymer exhibits the requisite properties described herein. Accordingly, as used herein, the terms "core" and "shell" refer to the polymeric content of the inside and the outside of the particle, respectively, and the use of said terms should not be construed as meaning that the disclosed polymer particles will necessarily exhibit a distinct interface between the polymers of the inside and the outside of the particle.

In some embodiments the staged core-shell polymer particle can be in a form in which the core portion is completely coated or encapsulated within the shell portion. In other embodiments the core-shell polymer particle can be in a form in which the core portion is only partly coated or encapsulated. It is also to be understood that in describing the "core polymers" and the "shell polymers" of the disclosed staged core-shell polymers there can be a significant amount of interpenetration of the polymers residing in the core and shell of the polymer particles. Thus, the "core polymers" can extend somewhat into the shell of the particle forming a domain in the shell particle, and vice versa.

The terms "core polymers" and "shell polymers" and like terminology are employed herein to describe the polymeric material in the named portion of the polymeric particle in a general way without attempting to identify any particular polymers as strictly "shell" or strictly "core" polymers.

As used herein, the term "(meth)acrylic" acid is meant to include both acrylic acid and methacrylic acid. Similarly, the term "alkyl (meth)acrylate" as used herein is meant to include alkyl acrylate and alkyl methacrylate.

The term "aqueous" as applied to formulations or media means that water is present in an amount sufficient to at least swell or dissolve the multi-purpose polymer in the composition into which it is formulated.

The alkali-swellable core-shell polymers of the present invention provide desirable rheological properties to aqueous formulations having a pH in the range of 2-12, or 3-10, or 4.5-10, said formulations being selected from personal care formulations, health care formulations, agricultural formulations, paint formulations, coating formulations, laundry and fabric care formulations, household care formulations, and industrial and institutional care formulations, and formulations for use in electronics industries, and formulations for use in construction industries. The alkali-swellable core-shell polymers of the present invention are useful in aqueous systems as well as in compositions containing one or more surfactants (e.g., anionic, cationic, amphoteric, non-ionic, and/or combinations of any two or more thereof). When used in personal care formulations that are hair styling formulations, in some embodiments the alkali-swellable core-shell polymers can also provide hair setting efficacy. In some embodiments the alkali-swellable core-shell polymers are useful thickeners in products containing active acid components and are useful thickeners and emulsifiers for emulsions (creams, lotions). In addition to thickening, in some embodiments the alkali-swellable core-shell polymers are useful film formers, spreading aids and deposition aids for products containing surfactants, colorants, hair and skin conditioners, silicones, monoquaternium compounds, polyquaternium compounds, anti-dandruff agents, anti-aging, anti-wrinkle, anti-pigment anti-cellulite, anti-acne, vitamins, analgesics, anti-inflammatory compounds, self-tanning agents, hair growth promoting agents, UV protecting agents, skin lighteners, vegetable, plant and botanical extracts, antiperspirants, antioxidants, deodorants, hair fixative polymers, emollient oils, and combinations thereof.

In some preferred embodiments, in addition to the desirable rheological properties as described above, the alkali-swellable core-shell polymers as disclosed herein also impart desirable clarity properties, as measured in units of turbidity. Aqueous compositions of the rheology modifiers disclosed herein can have a turbidity value of ≤1000 NTU in one aspect, ≤500 NTU in another aspect, ≤200 NTU in another aspect, 100 NTU in another aspect, and ≤50 NTU in a further aspect as measured in a thickened aqueous polymer composition comprising about 2% by weight polymer (active polymer solids) and the remainder water, and wherein the pH of the thickened composition is about 7.

As used herein, the term "rheological properties" and grammatical variations thereof includes without limitation such properties as viscosity, increase or decrease in viscosity in response to shear stress, and flow characteristics; gel properties such as stiffness, resilience, flowability, and the like; foam properties such as foam stability, foam density, ability to hold a peak, and the like; suspension properties such as yield value; and aerosol properties such as ability to form aerosol droplets when dispensed from propellant-based or mechanical pump-type aerosol dispensers; the flow of a liquid through a pump dispenser; or any quality or property that can be measured with a viscometer or a rotational or extensional rheometer. In some preferred embodiments, aqueous compositions of the rheology modifers disclosed herein will have yield values sufficient to support suspensions of aesthetic and cosmeceutical beads and particles, gaseous bubbles, exfoliants, and the like.

The term "aesthetic property" and grammatical variations thereof as applied to compositions refers to visual and tactile psychosensory product properties, such as color, clarity, smoothness, tack, lubricity, texture, conditioning and feel, and the like.

Here, as well as elsewhere in the specification and claims, individual numerical values (including carbon atom numerical values), or limits, can be combined to form additional non-disclosed and/or non-stated ranges.

The headings provided herein serve to illustrate, but not to limit the application in any way or manner.

Core-Shell Polymer

Alkali-swellable rheology modifiers for use in aqueous compositions comprise core-shell polymers, the shell comprising one or more copolymer layers, wherein at least one shell copolymer layer is an at least partially cross-linked polymer containing a mole percent of crosslinking agent greater than the mole percent of crosslinking agent in the core polymer, with the proviso that if the mole percent of crosslinking agent in the core is zero, then (a) the core is greater than 60% by weight of the core-shell polymer, and/or (b) the core contains associative monomer, and/or (c) at least one shell copolymer layer contains associative monomer, and/or (d) the at least one shell copolymer layer that is at least partially cross-linked comprises greater than 3 mol % crosslinking agent, based on the moles of monomers in that shell copolymer layer not counting the crosslinking agent. The core-shell polymers can include multiple shell copolymer layers, which can be the same as or different from the core layer and from each other with respect to both the type and proportions of monomers in the polymer backbone. The multiple shell copolymer layers can have any mole percent of crosslinking agent, as long as the core (first stage) polymer has a mole percent of crosslinking agent less than at least one of the crosslinked shell copolymer layer (subsequent stage) copolymers.

In one aspect, the core-shell polymer comprises from about 1% to about 95% by weight of the one or more shell copolymer layers, based on the total weight of the core-shell polymer. In one embodiment the core-shell polymer comprises about 5 wt % to about 60 wt % of the one or more shell copolymer layers, in one embodiment about 10 wt % to about 40 wt % of the one or more shell copolymer layers, and in one embodiment about 15 wt % to about 35 wt % of the one or more shell copolymer layers, in each case based on the total weight of the core-shell polymer, with the balance of the polymer being the core polymer. In one embodiment, if the core polymer comprises zero crosslinker and there is no associative monomer present in any core or shell copolymer layer, then the core is greater than 60 wt % and up to 95 wt % of the core-shell polymer.

Monomer Components

The core polymer is polymerized from a monomer composition comprising a) one or more non-associative anionic ethylenically unsaturated monomers; b) one or more hydrophobic ethylenically unsaturated monomers; c) optionally one or more nonionic ethylenically unsaturated monomers; d) optionally one or more associative monomers; and e) optionally one or more crosslinking agents. The one or more shell copolymer layers are each polymerized from a monomer composition comprising a) one or more non-associative anionic ethylenically unsaturated monomers; b) one or more hydrophobic ethylenically unsaturated monomers; c) optionally one or more nonionic ethylenically unsaturated monomers; d) optionally one or more associative monomers; and e) optionally one or more crosslinking agents, as long as at least one shell copolymer layer includes one or more crosslinking agents. The one or more crosslinking agents will be present in the monomer composition of at least one of the shell copolymer layers, and will be optionally present in the core monomer composition, as long as there is more crosslinking agent in at least one shell copolymer layer than in the core polymer.

Anionic Monomers

As used herein, the term "anionic ethylenically unsaturated monomer" means an ethylenically unsaturated monomer which is capable of developing a negative charge when the polymer is in an aqueous solution, and which anionic monomer is not an associative monomer, as defined below. These anionic ethylenically unsaturated monomers can include, but are not limited to, acrylic acid, methacrylic acid, 2-ethylacrylic acid, α-chloro-acrylic acid, α-cyano acrylic acid, β-methyl-acrylic acid (crotonic acid), α-phenyl acrylic acid, β-acryloxy propionic acid, sorbic acid, α-chloro sorbic acid, angelic acid, 2-carboxyethyl (meth)acrylate, cinnamic acid, p-chloro cinnamic acid, (-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, muconic acid, 2-acryloxypropionic acid, 2-acrylamido-2-methyl propane sulfonic acid, vinyl sulfonic acid, sodium methallyl sulfonate, sulfonated styrene, allyloxybenzene sulfonic acid, and vinyl phosphonic acid. Combinations of anionic ethylenically unsaturated monomers can also be used. In one embodiment, the anionic ethylenically unsaturated monomer may preferably be methacrylic acid, maleic acid, acrylic acid, itaconic acid, 2-acrylamido-2-methyl propane sulfonic acid or mixtures thereof. In one embodiment, most preferably the anionic ethylenically unsaturated monomer is methacrylic acid or acrylic acid, or combinations thereof.

In one aspect, the amount of the anionic ethylenically unsaturated monomer set forth under first monomer component a) ranges from about 10 mol % to about 90 mol %, from about 20 mol % to about 80 mol % in another aspect, and from about 30 mol % to about 70 mol %, or in still another aspect is greater than 10 mol %, or at least 15 mol %, or at least 20 mol %, or at least 30 mol %, or at least 40 mol %, or at least 50 mol % in the core polymer or shell copolymer layer in which the anionic ethylenically unsaturated monomer is used, in each case the mol % being based on the total moles of monomers present in that stage not including the crosslinking agent.

Hydrophobic Monomers

As used herein, the term "hydrophobic ethylenically unsaturated monomer" means a monomer that is hydrophobic and enables the formation of an emulsion system when reacted with the cationic ethylenically unsaturated monomer. For purposes of this application, a hydrophobic ethylenically unsaturated monomer can be sparingly soluble in water but has a water solubility of less than 6 grams per 100 mls of water at 25° C., or less than 3 grams per 100 mls of water at 25° C., preferably less than 2 grams per 100 mls of water at 25° C., and most preferably less than 1.6 gram per 100 mls of water at 25° C. These hydrophobic monomers may contain linear or branched alk(en)yl, cycloalkyl, aryl, or alk(en)aryl moieties. Suitable hydrophobic ethylenically unsaturated monomers include $C_1$-$C_{32}$ alkyl esters of acrylic and methacrylic acid including methyl (meth)acrylate, ethyl (meth)acrylate, n-propyl (meth)acrylate, iso-propyl (meth) acrylate, n-butyl (meth)acrylate, t-butyl (meth)acrylate, iso-butyl (meth)acrylate, n-amyl (meth)acrylate, iso-amyl (meth)acrylate, hexyl (meth)acrylate,octyl (meth)acrylate, decyl (meth)acrylate, benzyl (meth)acrylate, phenyl (meth) acrylate, benzyl ethoxylate (meth)acrylate, phenyl ethoxylate (meth)acrylate, 6-hydroxyhexyl (meth)acrylate, and 10-hydroxydecyl (meth)acrylate, 2-ethylhexyl (meth)acrylate, 2-butyloctyl (meth)acrylate, 2-hexyldecyl (meth)acrylate, 2-octyldodecyl (meth)acrylate, 2-decyltetradecyl (meth)acrylate, 2-dodecylhexadecyl (meth)acrylate, behenyl (meth)acrylate, lauryl (meth)acrylate, stearyl (meth)acrylate; and $C_4$-$C_{32}$ alkyl amides of acrylic and methacrylic acid, including tertiary butyl (meth)acrylamide, t-octyl (meth)acrylamide, 2-ethylhexyl (meth)acrylamide, n-octyl (meth)acrylamide, lauryl (meth)acrylamide, stearyl (meth) acrylamide, and behenyl (meth)acrylamide. Other suitable hydrophobic monomers include styrene, α-methyl styrene, vinyl toluene, t-butyl styrene, iso-propyl styrene, and p-chlorostyrene; vinyl acetate, vinyl butyrate, vinyl caprolate, vinyl valerate, vinyl hexanoate, vinyl octanoate, vinyl nonanoate, vinyl decanoate, vinyl neodecanoate, vinyl laurate, vinyl caprolactam, (meth)acrylonitrile, butadiene, isobutylene, isoprene, vinyl chloride, vinylidene chloride, 1-allyl naphthalene, 2-allyl naphthalene, 1-vinyl naphthalene, 2-vinyl naphthalene, All of the foregoing monomers may be used in any combination thereof.

Preferred are ethyl (meth)acrylate, methyl (meth)acrylate, 2-ethylhexyl acrylate, n-butyl (meth)acrylate, iso-butyl (meth)acrylate, t-butyl (meth)acrylate, vinyl acetate, tertiary butyl acrylamide and combinations thereof. In an embodiment, ethyl acrylate, methyl acrylate, methyl methacrylate, vinyl acetate, butyl acrylate and combinations thereof are preferred.

Exemplary alkyl (meth)acrylate monomers set forth under monomeric component b) include methyl (meth)acrylate, ethyl (meth)acrylate, n-propyl (meth)acrylate, iso-propyl (meth)acrylate, n-butyl (meth)acrylate, isobutyl (meth)acrylate, t-butyl (meth)acrylate, n-amyl (meth)acrylate, iso-amyl (meth)acrylate, and mixtures thereof. In an embodiment, ethyl acrylate is preferred.

In one aspect, the hydrophobic ethylenically unsaturated monomers set forth under the second monomer component b) are utilized in an amount ranging from about 10 mol % to about 90 mol %, from about 20 mol % to about 80 mol % in another aspect, and from about 30 mol % to about 70 mol % in still another aspect, or in still another aspect is at least 10 mol %, or at least 15 mol %, or at least 20 mol %, or at least 30 mol %, or at least 40 mol %, or at least 50 mol % in the core polymer or shell copolymer layer in which the hydrophobic ethylenically unsaturated monomer is used, in each case the mol % being based on the total moles of monomers present in that stage not including the crosslinking agent. In one embodiment the hydrophobic ethylenically unsaturated monomer is present at 20-30 mol %, based on the total moles of monomers present in that stage not including the crosslinking agent.

Optional Nonionic Ethylenically Unsaturated Monomers

As used herein, the term "nonionic ethylenically unsaturated monomer" means an ethylenically unsaturated monomer which does not introduce a charge into the core-shell polymers, and which is neither a hydrophobic ethylenically unsaturated monomer nor an associative monomer nor a crosslinker, each as defined herein. These nonionic ethylenically unsaturated monomers include, but are not limited to, acrylamide, methacrylamide, N—$C_1$-$C_3$alkyl(meth)acrylamides and N,N—$C_1$-$C_3$dialkyl(meth)acrylamides such as N-methylmethacrylamide, N-ethylacrylamide, N-propylacrylamide, N-isopropylacrylamide, N,N-dimethylacrylamide, and N,N-dimethylmethacrylamide; vinyl morpholine, vinyl pyrrolidone, vinyl propionate, vinyl butanoate, ethoxylated alkyl, alkaryl or aryl monomers such as methoxypolyethylene glycol (meth)acrylate, allyl glycidyl ether, allyl alcohol, glycerol (meth)acrylate, $C_1$ to $C_4$ hydroxyalkyl esters of (meth)acrylic acid, and others. Non-ionic ethylenically unsaturated monomers include (poly) $C_1$-$C_4$alkoxylated (meth)acrylates such as poly(ethylene glycol) (meth)acrylate and poly(propylene glycol) (meth) acrylate where n=1 to 100, preferably 3-50, and most preferably 5-20, ethoxylated $C_1$-$C_4$alkyl, $C_1$-$C_4$alkaryl or aryl monomers. In one aspect the optional nonionic ethylenically unsaturated monomer component c) is methoxypolyethylene glycol (meth)acrylate. The nonionic monomers can be used in any combination.

The optional $C_1$ to $C_4$ hydroxyalkyl esters of (meth) acrylic acid can include hydroxyethyl (meth)acrylate, hydroxypropyl (meth)acrylate, hydroxybutyl (meth)acrylate, and (butane diol mono(meth)acrylate). In one aspect the hydroxyalkyl ester of component c) is selected from 2-hydroxyethyl (meth)acrylate, 2-hydroxypropyl (meth)acrylate and 2-hydroxybutyl (meth)acrylate.

In one aspect, the optional nonionic ethylenically unsaturated monomer, when present, is present in ranges from about 10 mol % to 90 mol %, from about 20 mol % to about 80 mol % in another aspect, and from about 30 mol % to about 70 mol % in another aspect, based on the monomers present in the core polymer or shell copolymer layer in which the optional nonionic ethylenically unsaturated monomer is used, in each case the mol % being based on the total moles of monomers present in that stage not including the crosslinking agent.

Associative Monomers

As used herein, the term associative monomer is intended to mean an ethylenically unsaturated monomer containing a hydrophobe and a spacer moiety which allows the hydrophobe to be sufficiently far away from the backbone of the polymer to form hydrophobic associations in aqueous solutions, and wherein the hydrophobe comprises at least six carbon atoms. The spacer moieties are usually ethoxylate groups but any other group that extends the hydrophobe away from the backbone of the polymer may be used. The hydrophobes with a spacer moiety include, but are not limited to, alcohol ethoxylates, alkylphenoxy ethoxylates, propoxylated/butoxylated ethoxylates, ethoxylated silicones and the like. In an embodiment, the preferred hydrophobes with spacer moieties include alcohol ethoxylates and/or alkylphenoxy ethoxylates. In another embodiment, alcohol ethoxylates containing alcohols with carbon chain lengths of 6 to 40 and 6 to 100 moles of ethoxylation are more preferred. In yet another embodiment, alcohol ethoxylates containing alcohols with carbon chain lengths of 12 to 22 and 15 to 30 moles of ethoxylation are particularly preferred. The hydrophobes may be linear or branched alk(en)yl, cycloalkyl, aryl, alk(en)aryl or an alkoxylated derivative. In an embodiment, the most preferred hydrophobes are linear or branched alcohols and amines containing 12 to 32 carbons. The associative monomer may contain an ethylenically unsaturated monomer covalently linked to the hydrophobe. In an embodiment, the ethylenically unsaturated monomer part of the associate monomer preferably is a (meth)acrylate, itaconate and/or maleate which contains ester linking groups. However, the associative monomer may also contain amide, urea, urethane, ether, alkyl, aryl and other suitable linking groups. The hydrophobe may be an alkylamine or dialkylamine ethoxylate. In an embodiment, the (meth)acrylate group is most preferred. In another embodiment, preferred associative monomers are $C_{12-32}$ $(EO)_{10-30}$ meth(acrylates) or $C_{12-32}(EO)_{10-30}$ itaconates or or $C_{12-32}(EO)_{10-30}$ maleates.

In one embodiment, the associative monomer has the structure of formula (I)

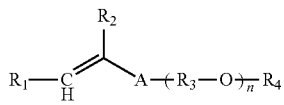
(I)

wherein $R_1$ is selected from —H, —$CH_3$, —COOH, or —$CH_2COOH$;

A is selected from —$CH_2C(O)O$—, —C(O)O—, —O—, —$CH_2O$—, —$CH_2C(O)N$—, —C(O)N—, —$CH_2$—, —O—C(O)—, —NHC(O)O—, —NHC(O)NH—, —$C_6H_4$ ($R_3$)—NH—C(O)—O—, —$C_6H_4(R_5)$—NH—C(O)—NH—, —C(O)O—$CH_2$—CH($CH_2OH$)—O—, —C(O)O—$CH_2$—CH($CH_2OH$)—NH—, —C(O)O—$CH_2$—CH—$CH_2$ (OH)—O—, —C(O)O—$CH_2$—CH—$CH_2$(OH)—NH—, —$CH_2$—O—$CH_2$—CH($CH_2OH$)—O—, —$CH_2$—O—$CH_2$—CH—$CH_2$(OH)—O—, —$CH_2$—O—$CH_2$—CH ($CH_2OH$)—NH—, or —$CH_2$—O—$CH_2$—CH—$CH_2$ (OH)—NH—;

$(R_3—O)_n$ is a polyoxyalkylene, which is a homopolymer, a random copolymer, or a block copolymer of $C_2$ to $C_4$ oxyalkylene units, wherein each $R_3$ is independently selected from —$C_2H_4$—, —$C_3H_6$—, —$C_4H_8$—, or a mixture thereof, and n is an integer in the range of about 5 to about 250, preferably, n is 5-100, more preferably 10-50 and most preferably 15-30;

$R_4$ is selected from $C_6-C_{36}$ linear or branched, saturated or unsaturated alk(en)yl or alk(en)aryl, preferably $C_8-C_{32}$ linear or branched alk(en)yl, more preferably $C_{10}-C_{22}$ linear alk(en)yl or $C_{10}-C_{32}$ branched alk(en)yl; and $R_5$ is —$CH_2$— or —(C)($CH_3$)$_2$—.

Suitable associative monomers include methacrylate and itaconate esters of a hydrophilic ethoxylate chain and a hydrophobic alkyl chain.

In one embodiment, the associative monomer is an alkyl ethoxylate methacrylate ester having the structure of formula I(A):

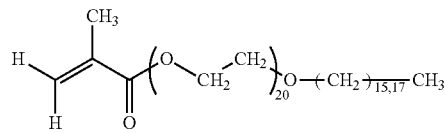

In one embodiment the associative monomer is an itaconate-based associative monomer such as cetyl ethoxylate itaconate, behenyl ethoxylate itaconate, or stearyl ethoxylate itaconate having the structure of formula I (B, C, D respectively)

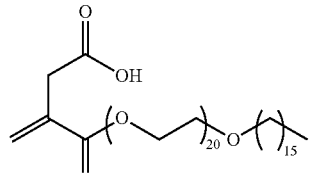

B - Cethyl ethoxylate (20) itaconate

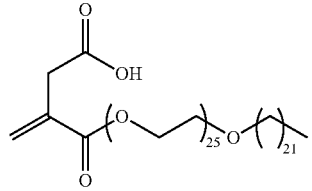

C - Behenyl ethoxylate (25) itaconate

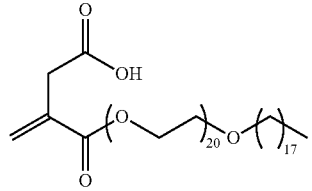

D - Stearyl ethoxylate (20) itaconate

In one aspect, the optional associative monomers set forth under the monomer component d), when present, are utilized in an amount ranging from about 0.01 mol % to about 3 mol %, or from about 0.05 mol % to about 2 mol %, or from about 0.1 mol % to about 1 mol % in still another aspect, in the core polymer or shell copolymer layer in which the associative monomer is used, in each case the mol % being based on the total moles of monomers present in that stage not including the crosslinking agent.

Crosslinking Agents

In one aspect, at least one shell copolymer layer of the core-shell polymer includes a crosslinking agent such that the layer containing the crosslinking agent is a partially or substantially-crosslinked network. The core also can contain crosslinking agent, whereby the core will be a partially or substantially-crosslinked network, as long as the mole percent of crosslinking agent in the core (first stage) polymer is less than the mole percent of crosslinking agent in at least one of the shell (subsequent stage) copolymer layers that includes a crosslinking agent.

The crosslinking agent can be selected from one or more of a crosslinking monomer having two or more carbon-carbon double bonds, or a polyfunctional crosslinking compound that reacts with pendant functional groups on the polymer.

Exemplary crosslinking monomers include di(meth)acrylate compounds such as ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth) acrylate, neopentyl glycol di(meth)acrylate, 1,9-nonanediol di(meth)acrylate, 2,2'-bis(4-(acryloxy-propyloxyphenyl) propane, 2,2'-bis(4-(acryloxydiethoxy-phenyl)propane, and zinc acrylate (i.e., $2(C_3H_3O_2)Zn^{++}$); tri(meth)acrylate compounds such as, trimethylolpropane tri(meth)acrylate, trimethylolethane tri(meth)acrylate, trimethyl(ethoxylate)propane tri(meth)acrylate, and tetramethylolmethane tri(meth) acrylate; tetra(meth)acrylate compounds such as ditrimethylolpropane tetra(meth)acrylate, tetramethylolmethane tetra(meth)acrylate, and pentaerythritol tetra(meth) acrylate; hexa(meth)acrylate compounds such as dipentaerythritol hexa(meth)acrylate; allyl compounds such as allyl (meth)acrylate, diallyl phthalate, diallyl itaconate, diallyl fumarate, and diallyl maleate; polyallyl ethers of sucrose having from 2 to 8 alkyl groups per molecule, polyallyl ethers of pentaerythritol such as pentaerythritol diallyl ether, pentaerythritol triallyl ether, and pentaerythritol tetraallyl ether; polyallyl ethers of trimethylolpropane such as trimethylolpropane diallyl ether and trimethylolpropane triallyl ether. Other suitable polyunsaturated compounds include divinyl glycol, divinyl benzene, and N,N'-methylenebisacrylamide.

In another aspect, suitable polyunsaturated monomers can be synthesized via an esterification reaction of a polyol made from ethylene oxide or propylene oxide or combinations thereof with unsaturated anhydride such as maleic anhydride, citraconic anhydride, itaconic anhydride, or an addition reaction with unsaturated isocyanate such as 3-isopropenyl-α-α-dimethylbenzene isocyanate.

Exemplary polyfunctional crosslinking compounds include polyhaloalkanols such as 1,3-dichloroisopropanol and 1,3-dibromoisopropanol; sulfonium zwitterions such as the tetrahydrothiophene adduct of novolac resins; haloepoxyalkanes such as epichlorohydrin, epibromohydrin, 2-methyl epichlorohydrin, and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers, bisphenol A-epichlorohydrin epoxy resins and mixtures of the foregoing. Mixtures of two or more of the foregoing polyfunctional compounds can also be used.

The amount of crosslinking agent in each layer will be selected depending on the desired properties the core-shell polymer.

In some embodiments in which at least one associative monomer is present during at least one of the core-shell synthesis stages and/or there is at least one crosslinking agent present during the core (first) synthesis stage, the molar percentage of crosslinking agent in a given stage, when present, is about 0.01 mol % to about 20 mol % based on the monomers present in that stage not including the crosslinking agent, preferably about 0.03 mol % to about 15 mol % based on the monomers present in that stage not including the crosslinking agent, and more preferably about 0.05 mol % to about 10 mol % based on the monomers present in that stage not including the crosslinking agent, and most preferably from about 0.05 mol % to about 7 mol % based on the total moles of monomers present in that stage not including the crosslinking agent.

In another embodiment in which no associative monomer is present in any stage of the core-shell particle synthesis, no crosslinking agent is present during the core (first) stage synthesis, and the mass of the core (first stage) comprises more than 60% of the mass of the core-shell particle, the crosslinking agent content of at least one shell (subsequent stage) polymer can be present during the synthesis of that stage in an amount ranging from about 0.05 mol % to about 20 mol % based on the moles of the monomers in that shell stage not including the crosslinking agent, preferably from about 0.05 mol % to 10 mol % based on the moles of the monomers in that shell stage not including the crosslinking agent, and most preferably from about 0.1 mol % to about 10 mol % based on the total moles of monomers in that shell stage not including the crosslinking agent.

In yet another embodiment in which no associative monomer is present in any stage of the core-shell particle synthesis, no crosslinking agent is present during the core (first) stage synthesis, and the mass of the core (first stage) comprises less than 60% of the mass of the core-shell particle, the crosslinking agent of at least one shell (subsequent stage) polymer can be present during the synthesis of that stage in an amount ranging from about 3 mol % to about 20 mol % based on the moles of the monomers in that shell stage not including the crosslinking agent, preferably from about 3 mol % to 15 mol % based on the moles of monomers in that shell stage not including the crosslinking agent, and most preferably from about 3 mol % to about 10 mol % based on the moles of monomers in that shell stage not including the crosslinking agent.

Chain Transfer Agents

Chain transfer agents can be used in any stage of the core-shell polymerization process. The chain transfer agent can be any chain transfer agent which reduces the molecular weight of the disclosed staged polymers. Suitable chain transfer agents include, but are not limited to, thio and disulfide containing compounds, such as $C_1$-$C_{18}$ alkyl mercaptans, $C_1$-$C_{18}$ alkyl mercaptoalcohols, mercaptocarboxylic acids, mercaptocarboxylic esters, thioesters, $C_1$-$C_{18}$ alkyl disulfides, arylsulfides, polyfunctional thiols such as trimethylolpropane-tris-(3-mercaptopropionate), pentaerythritol-tetra-(3-mercaptopropionate), pentaerythritol-tetra-(thioglycolate), and pentaerythritol-tetra-(thiolactate), dipentaerythritol-hexa-(thioglycolate), and the like; phosphites and hypophosphites; haloalkyl compounds, such as carbon tetrachloride, bromotrichloromethane, and the like; and catalytic chain transfer agents such as, for example, cobalt complexes (e.g., cobalt (II) chelates).

In one aspect, the chain transfer agent is selected from n-dodecyl mercaptan, methyl mercaptopropionate, and 3-mercaptopropionic acid, 2-mercaptoethanol, combinations thereof and the like, octyl mercaptan, t-dodecyl mercaptan, hexadecyl mercaptan, octadecyl mercaptan, isooctyl 3-mercaptopropionate, butyl 3-mercaptopropionate, butyl thioglycolate, isooctyl thioglycolate, and dodecyl thioglycolate.

When utilized, the chain transfer agent can be present in an amount less than 0.75 mol % based on the monomers present in that stage not including the crosslinking agent in one aspect, less than 0.5 mol % based on the monomers present in that stage not including the crosslinking agent in another aspect, and less than 0.1 mol % based on the monomers present in that stage not including the crosslinking agent in a further aspect.

Core-Shell Polymer Preparation

The core-shell polymers disclosed herein comprise at least two polymers synthesized sequentially via free radical emulsion polymerization techniques known to the art.

The core polymer is synthesized in a first emulsion polymerization step from a monomer composition comprising a) one or more anionic ethylenically unsaturated monomers; b) one or more hydrophobic ethylenically unsaturated monomers; and optionally c) one or more nonionic ethylenically unsaturated monomers, and/or d) one or more associative monomers, and/or e) a one or more crosslinking agent, all as disclosed above. A chain transfer agent also can be used.

In one embodiment, termed a monomer pre-emulsion, the core monomer composition is emulsified in a water and surfactant mixture in a first vessel before being added to the reactor where emulsion polymerization takes place. In another embodiment, termed a monomer mixture, the core monomer composition has no added water or surfactant before being adding to the reactor where emulsion polymerization takes place.

The core monomers are polymerized in the presence of a suitable free radical forming initiator to provide an emulsion of a core polymer. In one embodiment, the core polymerization preferably begins with a "seed" process in which seed polymer particles are formed that serve as loci for subsequent polymerization.

The monomer composition is introduced to an optionally surfactant containing aqueous charge in a reactor either as a monomer pre-emulsion or a separate monomer mixture and aqueous surfactant solution. When a monomer mixture is used, an aqueous surfactant solution can be added to the reactor at the same time as or directly after the addition of the monomer mixture. The reactor contents are stirred and a small amount of free-radical initiator is added to the reactor to initiate the formation of seed particles.

Upon completion of the seed stage, the monomer composition required to complete the core may be added as a monomer pre-emulsion concurrent with an initiator feed, or as a monomer mixture added concurrently with an aqueous surfactant solution feed and an initiator feed. Alternatively, the initiator can be added prior to the addition of the monomer composition to the reactor.

Next, a shell polymer is formed in a second polymerization step. The monomer composition required to form the shell may be added as a monomer pre-emulsion concurrent with an initiator feed, or as a monomer mixture added concurrently with an aqueous surfactant solution feed and an initiator feed. Alternatively, the initiator can be added prior to the addition of the monomer composition to the reactor. The end-product is a two stage polymer comprising the core surrounded or partially surrounded by a shell, wherein the mole percent of crosslinking agent in the core is less than the mole percent of crosslinking agent in the shell.

In an alternative embodiment of the method of making the core-shell polymer, only a portion of the full amount of surfactant to be used is initially present in the reactor, and the remainder is added as a concurrent stream along with the stream of monomer composition and the stream of initiator, during all steps of the polymerization.

Optionally, further successive free radical emulsion polymerization stages can be run to obtain multi-layer polymer morphologies such that successive polymer stages differ at least by the mole percent of crosslinking agent present in that stage, subject to the proviso that the core or first stage polymer must have a mole percent of crosslinking agent that is less than at least one of the shell polymer layers. In a stage where it is desired to have a linear polymer, the emulsion polymerizable monomer composition will be devoid of crosslinking agent, and in a stage where it is desired to have a crosslinked polymer the emulsion polymerizable monomer composition will comprise a crosslinking agent.

To obtain the desired properties for any particular end-use application, in preparing the core-shell polymers as disclosed herein, it is possible to adjust any of (i) the relative mole ratios of the individual monomers, (ii) the mass percent of each of the core and shell stages in the core-shell polymer, (iii) the choice of monomers, crosslinking agent, or associative monomers in any of the layers, (iv) the addition rate of monomer mixtures, surfactant solutions, and initiator solutions, and (v) the mole percentage of crosslinking agent in any of the layers, as long as the mole percent of crosslinking agent in the core (first stage) is less than the mole percent of crosslinking agent in at least one of the shell (subsequent stage) layers.

While the core-shell polymer is synthesized by successive emulsion polymerization steps to yield an aqueous polymer emulsion, it should be recognized that the core-shell polymer can be supplied in dried powder form if desired.

The emulsion polymerization can be carried out in a staged batch process, in a staged semi-batch monomer addition process or multi-step continuous process, or the polymerization can be initiated as a batch process and then the bulk of the monomers can be continuously staged into the reactor (seeded semi-batch process), as discussed above.

Typically, the emulsion polymerization reactions are carried out at a reaction temperature in the range of about 20 to about 99° C., however, higher or lower temperatures can be used.

The emulsion polymerization reactions can be performed in an aqueous or aqueous alcohol medium.

The surfactant can be added to the monomer composition to form a pre-emulsion, or the surfactant can be added directly to the polymerization reactor during the emulsion polymerization, or both. In one embodiment, the emulsion polymerization is carried out in the presence of surfactant ranging in the amount of about 0.01% to about 10% by weight in one aspect, from about 0.1% to about 5% in another aspect, and from about 0.3% to about 3% by weight in a further aspect, based on a total emulsion weight basis.

Suitable surfactants include anionic, nonionic, amphoteric, and cationic surfactants, as well as mixtures thereof. Most commonly, anionic and nonionic surfactants can be utilized as well as mixtures thereof.

Suitable anionic surfactants for facilitating emulsion polymerizations are well known in the art and include, but are not limited to, sodium lauryl sulfate, sodium dodecyl benzene sulfonate, sodium ($C_6$-$C_{16}$) alkyl phenoxy benzene sulfonate, disodium ($C_6$-$C_{16}$) alkyl phenoxy benzene sulfonate, disodium ($C_6$-$C_{16}$) di-alkyl phenoxy benzene sulfonate, disodium laureth-3 sulfosuccinate, sodium dioctyl sulfosuccinate, sodium di-sec-butyl naphthalene sulfonate, disodium dodecyl diphenyl ether sulfonate, disodium n-octadecyl sulfosuccinate, phosphate esters of branched alcohol ethoxylates, and the like.

Nonionic surfactants suitable for facilitating emulsion polymerizations are well known in the polymer art, and include, without limitation, linear or branched alcohol ethoxylates, C$_8$to C$_{12}$ alkylphenol alkoxylates, such as octylphenol ethoxylates, polyoxyethylene polyoxypropylene block copolymers, and the like. Other useful nonionic surfactants include C$_8$to C$_{22}$ fatty acid esters of polyoxyethylene glycol, mono and diglycerides, sorbitan esters and ethoxylated sorbitan esters, C$_8$to C$_{22}$ fatty acid glycol esters, block copolymers of ethylene oxide and propylene oxide having an HLB value of greater than about 12, ethoxylated octylphenols, and combinations thereof. In another embodiment, linear alcohol alkoxylates include polyethylene glycol ethers of cetearyl alcohol (a mixture of cetyl and stearyl alcohols) sold under the trade names PLURAFAC® C-17, PLURAFAC® A-38 and PLURAFAC® A-39 by BASF Corp. In still another embodiment, polyoxyethylene polyoxypropylene block copolymers include copolymers sold under the trade names PLURONIC® F127, and PLURONIC® L35 by BASF Corp.

Other suitable nonionic surfactants include, but are not limited to, Ethoxylated linear fatty alcohols such as DISPONIL® A 5060 (Cognis), Ethal LA-23 and Ethal LA-50 (Ethox Chemicals), branched alkyl ethoxylates such as GENAPOL® X 1005 (Clariant Corp.), secondary $C_{12}$ to 014 alcohol ethoxylates such as TERGITOL® S15-30 and S15-40 (Dow Chemical Co.), ethoxylated octylphenol-based surfactants such as TRITON® X-305, X-405 and X-705 (Dow Chemical Co.), IGEPAL® CA 407, 887, and 897 (Rhodia, Inc.), ICONOL® OP 3070 and 4070 (BASF Corp.), SYNPERONIC® OP 30 and 40 (Uniqema), block copolymers of ethylene oxide and propylene oxide such as PLURONIC® L35 and F127 (BASF Corp.), and secondary $C_{11}$ alcohol ethoxylates such as EMULSOGEN® EPN 407 (Clariant Corp.). Numerous other suppliers are found in the trade literature.

In addition, suitable surfactants are also described in *The Handbook of Industrial Surfactants* (Fifth Edition, by Michael and Irene Ash) which is hereby fully incorporated by reference.

The emulsion polymerization can be carried out in the presence of a suitable polymeric stabilizer. Suitable polymeric stabilizers (also known as protective colloids) for the emulsion polymerization process of this invention are water-soluble polymers, including, for example, synthetic polymers, such as polyvinyl alcohol, partially hydrolyzed polyvinyl acetate, polyvinylpyrrolidone, polyacrylamide, polymethacrylamide, carboxylate-functional addition polymers, polyalkyl vinyl ethers and the like; water-soluble natural polymers, such as gelatin, pectins, alginates, casein, starch, and the like; and modified natural polymers, such as methylcellulose, hydroxypropylcellulose, carboxymethylcellulose, allyl modified hydroxyethylcellulose, and the like. In some cases, it can be of advantage to use mixtures of a synthetic and a natural protective colloid, for example, a mixture of polyvinyl alcohol and casein. Further suitable natural polymers are mixed ethers such as methylhydroxyethylcellulose and carboxymethylmethylcellulose. Polymeric stabilizers can be utilized in amounts up to about 10 weight percent based on the total emulsion weight, or up to about 7.5 weight percent, or up to about 5 weight percent, or up to about 2.5 weight percent, or up to about 2 weight percent based on the total emulsion weight. In another embodiment, when utilized, a polymeric stabilizer is included in an amount in the range of about 0.001 weight percent to about 10 weight percent, or from about 0.01 weight percent to about 7.5 weight percent, or from about 0.1 weight percent to about 5 weight percent, or from about 0.5 weight percent to about 2.5 weight percent, or even from about 1 weight percent to about 2 weight percent, based on the total emulsion weight.

In a free radical emulsion polymerization, free radical initiators that generate a free radical during the polymerization process are utilized. As used herein, the initiating system is any free radical initiating system. The free radical initiators are present in an amount ranging from about 0.01 wt % to about 3 wt % based on total monomer weight. In an embodiment, the initiating system is soluble in water to at least 0.1 weight percent at 25° C. Suitable initiators include, but are not limited to, peroxides, azo initiators as well as redox systems, such as hydrogen peroxide and erythorbic acid, and metal ion based initiating systems. Initiators may also include both inorganic and organic peroxides, such as hydrogen peroxide, benzoyl peroxide, acetyl peroxide, and lauryl peroxide; organic hydroperoxides, such as cumene hydroperoxide and t-butyl hydroperoxide. In an embodiment, the inorganic peroxides, such as sodium persulfate, potassium persulfate and ammonium persulfate, are preferred. In another embodiment, the initiators comprise metal ion based initiating systems including Fe and hydrogen peroxide, as well as Fe in combination with other peroxides.

Organic peracids such as peracetic acid can be used. Peroxides and peracids can optionally be activated with reducing agents, such as sodium bisulfite, sodium formaldehyde, or ascorbic acid, transition metals, hydrazine, and the like. Azo initiators, especially water soluble azo initiators, may also be used. Water soluble azo initiators include, but are not limited to, 2,2'-Azobis[2-(2-imidazolin-2-yl)propane]dihydrochloride, 2,2'-Azobis[2-(2-imidazolin-2-yl)propane]disulfate dihydrate, 2,2'-Azobis(2-methylpropionamidine)dihydrochloride, 2,2'-Azobis[N-(2-carboxyethyl)-2-methylpropionamidine]hydrate, 2,2'-Azobis{2-[1-(2-hydroxyethyl)-2-imidazolin-2-yl]propane}dihydrochloride, 2,2'-Azobis[2-(2-imidazolin-2-yl)propane], 2,2'-Azobis(1-imino-1-pyrrolidino-2-ethylpropane)dihydrochloride, 2,2'-Azobis{2-methyl-N-[1,1-bis(hydroxymethyl)-2-hydroxyethl]propionamide}, 2,2'-Azobis[2-methyl-N-(2-hydroxyethyl)propionamide] and others. Oil soluble, free radical producing agents, such as 2,2'-azobisisobutyronitrile, and the like, and mixtures thereof also can be used.

Optionally, other emulsion polymerization additives and processing aids which are well known in the emulsion polymerization art, such as auxiliary emulsifiers, solvents, buffering agents, chelating agents, inorganic electrolytes, polymeric stabilizers, biocides, antifoam agents, and pH adjusting agents can be included in the polymerization system.

In one aspect, an auxiliary emulsifying aid selected from an ethoxylated $C_{10}$ to $C_{22}$ fatty alcohol (or their mixtures) can be added to the polymerization medium. In one aspect, the fatty alcohol contains from about 5 to about 250 moles of ethoxylation, from about 8 to 100 moles in another aspect, and from about 10 to 50 moles in a further aspect. Exemplary ethoxylated fatty alcohols include lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and behenyl alcohol ethoxylate. In another aspect, suitable ethoxylated fatty alcohols include Ceteth-20, Ceteareth-20, and Steareth-20, Behenth-25, and mixtures thereof.

If employed, the amount of ethoxylated fatty alcohol can range from about 0.01% to 10% by weight in one aspect, from about 0.1% to about 5% by weight in another aspect, and from about 0.3% to about 3% by weight in a further aspect, based on a total weight of emulsion basis.

The following describes a typical two-stage polymerization. First a core stage monomer composition comprising a) one or more anionic ethylenically unsaturated monomers; b) one or more hydrophobic ethylenically unsaturated monomers; and optionally c) one or more nonionic ethylenically unsaturated monomers, and/or d) one or more associative monomers, and/or e) one or more crosslinking agents, and/or a chain transfer agent, all as disclosed above, is added to a first vessel with mixing and is added to a solution of emulsifying surfactant (e.g., anionic surfactant) in water to prepare a monomer pre-emulsion. Optional processing aids can be added as desired (e.g., auxiliary emulsifier(s)).

A polymerization reactor is charged with a desired amount of water, additional surfactant and optional processing aids. The polymerization reactor is equipped with attached inert gas inlet and feed pumps, and the reactor contents are maintained under inert atmosphere and heated with mixing agitation. The contents of the reactor are brought to a temperature in the range of about 55 to 98° C., and are maintained at those conditions for about an hour. A seed stage is performed in a manner consistent with the addition of monomer and surfactant by means of a pre-emulsion as described above. The desired amount of core stage monomer pre-emulsion is fed subsurface into the reactor, and a free radical initiator solution is fed separately and concurrently with the core stage monomer composition into the reactor contents over a period of about one half to two hours. During this time, the reaction temperature is controlled in the range of about 45 to about 95° C.

After a desired amount of the core monomer composition has been added to the reactor, the feed may be stopped and, if desired, an additional quantity of free radical initiator can optionally be added to the reactor. The resulting reaction mixture can be held at a temperature of about 45 to 95° C. for a time period sufficient to complete or substantially complete the polymerization reaction and obtain a first stage core polymer particle emulsion.

A shell stage monomer composition containing a desired complement of shell stage monomers and other components listed above for a core stage monomer composition, including a crosslinking agent, can be mixed in a separate vessel following the same procedures as outlined for formulating the core stage monomer composition.

Alternatively, to the first vessel containing remaining material from the core stage monomer composition, a crosslinking agent can be added and mixed with agitation to form a shell stage or second stage monomer composition. Additional shell stage monomers can be added into the composition if desired.

The shell stage or second stage monomers are metered into the polymerization reactor at a constant rate and mixed with the core polymer emulsion. Simultaneously with the shell stage monomer feed, a free radical initiator solution in an amount sufficient to reinitiate polymerization is metered into the reaction mixture, such that the shell stage or second stage monomers are polymerized in the presence of the core stage or first stage polymer. The temperature is then maintained at about 85° C. for about one half to two and a half hours or until polymerization is complete. Unreacted monomer can be eliminated by completing a monomer chase step, such as addition of more initiator or by adjusting and maintaining temperature for a period of time to maintain radical flux from thermal initiator residues, as is well known in the emulsion polymerization art. Typically, the staged core-shell polymer or staged polymer emulsion product has a total polymer solids content in the range of about 10 to about 45 weight percent. While the polymer is synthesized in an emulsion, it should be recognized that the staged core-shell polymer can be supplied in dried powder form if desired.

While a typical two-stage polymer process is generally described immediately above, multi-staged or multi-layered polymers can be formed through the sequential emulsion polymerization of monomer charges in the presence of polymer particles of a previously formed emulsion polymer.

Dried Rheology Modifier Compositions

In one aspect the rheology modifier compositions can be in the form of dried rheology modifiers. In one embodiment the rheology modifier composition can be dried by spray drying.

The present disclosure further relates to a method of making rheology modifier compositions, comprising blending the core-shell polymer with a spray drying adjuvant, and drying the resultant mixture.

In one aspect, spray-drying can be facilitated by the presence of a spray-drying adjuvant. In some embodiments, spray-drying adjuvant is derived from a natural renewable resource. The natural renewable resource can be a polysaccharide, such as a starch or cellulose. Alternatively, the spray drying adjuvant can be a derivative of a polyvinyl acetate. In some embodiments, the spray drying adjuvant is present in the emulsion polymer composition during the polymerization process. In some embodiments, spray drying adjuvant is blended into the emulsion polymerization product prior to spray drying.

The core-shell polymers that are emulsion polymerized as described above and then blended with a spray drying adjuvant polymer can be dried, preferably by spray drying, to provide dried rheology modifier compositions in the form of stable powders. The spray drying adjuvant may be a polysaccharide, suitable examples of which include starch and cellulose, and derivatives thereof. Other suitable spray drying adjuvants include derivatives of polyvinyl acetate such as polyvinyl alcohol, copolymers of polyvinyl alcohol/polyvinyl acetate, and other copolymers of polyvinyl alcohol. Spray drying adjuvants may be used to impart additional desirable textural and rheological properties to the formulations in which the dry rheology modifiers of the present application may be used.

The term "dried rheology modifier composition" as used herein means a composition comprising at least one core-shell polymer and at least one polysaccharide, the composition being in a dry form comprising less than 25 wt % water, in one embodiment less than 20 wt % water, in one embodiment less than 10 wt % water, in one embodiment less than 5 wt % water, in one embodiment less than 2 wt % water, in one embodiment less than 1 wt % water, in one embodiment less than 0.5 wt % water.

The polysaccharide component allows the resulting composition to be dried to produce a dried rheology modifier composition with less than 25 weight percent water. Without being bound by theory, it is believed that higher glass transition temperatures of the polysaccharide polymer make it easier to dry the rheology modifier composition. In one embodiment the polysaccharide polymer has a glass transition temperature of at least 50° C., in one embodiment at least 75° C., and in one embodiment at least 90° C.

The weight percent of the polysaccharide polymer or other spray drying adjuvant is at least about 20 wt % of the dried rheology modifier composition, preferably at least about 25 wt % of the dried rheology modifier composition, and most preferably at least about 30 weight % of the dried rheology modifier composition. The maximum weight percent of the polysaccharide polymer or other spray drying adjuvant is no more than about 90 wt % of the dried rheology modifier composition, in another embodiment preferably no more than about 85 wt % of the dried rheology modifier composition, and in yet another embodiment most preferably no more than about 80 wt % of the dried rheology modifier composition.

In yet another embodiment, the dried rheology modifier composition comprises a mixture of the products of at least two different core-shell copolymer compositions.

In yet another embodiment, the dried rheology modifier composition comprises more than one polysaccharide polymer or other spray drying adjuvant.

Optionally, prior to the drying step a second composition is added, the second composition comprising a second core-shell polymer and optionally a second polysaccharide polymer or other spray drying adjuvant, wherein each of the second core-shell polymer and the optional second polysaccharide polymer or other spray drying adjuvant of the second composition can be the same as or different from the at least one core-shell polymer and at least one polysaccharide polymer, respectively, of the initial polymer blend The particle size of the solid product may be adjusted using methods known in the art such as milling.

Spray-Drying Adjuvant Polymers

In one aspect, the rheology modifiers as disclosed herein can be blended with a spray drying adjuvant polymer before being spray dried. Suitable spray drying adjuvant polymers include polysaccharide polymers, which includes without limitation starch and starch derivatives, cellulose and cellulose derivatives, and gums; and polyvinyl acetate derivatives.

Polysaccharide Polymers

Polysaccharides useful as spray drying adjuvant polymers can be derived from plant, animal and microbial sources. Examples of such polysaccharides include starch, cellulose, gums (e.g., gum arabic, guar and xanthan), alginates, pectin, carrageenan, inulin and gellan, and derivatives of each of the foregoing. One skilled in the art will recognize that the polysaccharides may need to depolymerized or derivatized to be water soluble. For example a starch may need to be depolymerized to a molecular weight of 10 million or less to be water soluble. Similarly a cellulose may have to be derivatized, for example to a carboxymethyl cellulose, to be water soluble.

The weight average molecular weight of the polysaccharide based spray drying adjuvant polymers can be about 20,000,000 or less, or 10,000,000 or less, or about 1,000,000 or less, or about 100,000 or less, or about 10,000 or less.

Starch and Starch Derivatives

Starches include those derived from maize and conventional hybrids of maize, such as waxy maize and high amylose (greater than 40% amylose) maize, as well as other starches such as potato, tapioca, wheat, rice, pea, sago, oat, barley, rye, and amaranth, including conventional hybrids or genetically engineered materials. The starches can be of the native variety or a hybrid variety produced by traditional breeding programs or by artificial gene manipulation. These hybrids include but are not limited to waxy versions (starches with little or no amylose) and high amylose cultivars. Waxy starches are typically defined as having about 5% or less amylose and sometime containing about 2% or less amylose. In an embodiment, the waxy starches have about 95% or greater amylopectin. High amylose starches are defined as having about 40% or greater amylose (with the exception of pea starch which has a high amylose content of about 27% or greater amylose). In a further embodiment, the high amylose starches have an amylose content of about 60% or greater amylose. In addition, starches which have altered chain length and branch points are included in this application.

In an embodiment, the preferred polysaccharides are starches and starch derivatives, including, but not limited, to thermal and/or mechanically treated starch, oxidatively, hydrolytically or enzymatically degraded starches, and chemically modified starches. These preferred polysaccharides include maltodextrins, dextrin, pyrodextrins, oxidized starches, cyclodextrins and substituted cyclodextrins and higher molecular weight starches or derivatives thereof. In another preferred embodiment the preferred starches are waxy maltodextrins, waxy dextrins, waxy pyrodextrins, waxy oxidized starches, and higher molecular weight waxy starches or derivatives thereof. The most preferred starches are waxy maltodextrins. Chemical modification includes hydrolysis by the action of acids, enzymes, oxidizers or heat, esterification or etherification. The chemically modified starches, after undergoing chemical modification may be cationic, anionic, non-ionic or amphoteric or hydrophobically modified.

In an embodiment, the polysaccharide is a maltodextrin. Maltodextrins are polymers having d-glucose units linked primarily by α-1,4 bonds and a dextrose equivalent (DE') of about 20 or less. Dextrose equivalent is a measure of the extent of starch hydrolysis. It is determined by measuring the amount of reducing sugars in a sample relative to dextrose (glucose). The DE of dextrose is 100, representing 100% hydrolysis. The DE value gives the extent of hydrolysis (e.g., 10 DE is more hydrolyzed than 5 DE maltodextrin). Maltodextrins are available as a white powder or concentrated solution and are prepared by the partial hydrolysis of starch with acid and/or enzymes.

Suitable polysaccharides can further include corn syrups. Corn syrups are defined as degraded starch products having a DE of 27 to 95. Examples of specialty corn syrups include high fructose corn syrup and high maltose corn syrup. Although not strictly polymers, monosaccharides and oligosaccharides such as galactose, mannose, sucrose, maltose, fructose, ribose, trehalose, lactose, etc., can be used as spray drying adjuvants in the disclosed compositions and methods, and for purposes hereof are considered to fall within the scope of spray drying adjuvant polymers.

In an embodiment, the polysaccharide has a DE of about 65 or less, 45 or less, 20 or less, in another embodiment a DE of about 15 or less and in still another embodiment a DE of about 5 or less. In an embodiment, the polysaccharide has a DE with a range having a lower limit of at least about 1.

In one embodiment, the polysaccharides are pregelatinized starch and its derivatives. The pregelatinized starches suitable herein are those starches that have been treated with heat, moisture, or chemicals to disrupt the natural granular structure and render the starch soluble in water at below the gelatinization temperature of the native starch. For purposes of the application, pregelatinized starches are also referred to as cold water soluble starches (CWS) and the terms are used interchangeably. For a general review of how to prepare pregelatinized starches see (Starch; Chemistry and Technology, R. L. Whistler, second edition, Academic Press, Inc. New York, 1984 pages 670-673). Additionally these products can be prepared by co-jet cooking coupled to a spray drier (see Kasica et al. U.S. Pat. No. 5,571,552). The pregelatinization can be done by different methods including but not limited to drum-drying, spray cooking or extrusion. In addition to being pregelatinized the starches suitable for use herein can further be modified to contain anionic, cationic, non-ionic and reactive groups. Derivatives of these types are described in "Modified Starches: Properties and Uses" O. B. Wurzburg, CRC Press Boca Raton, Fla., 1986 chapters 3-9. The modified starches can be prepared in the granular form and then made cold water soluble or can be cooked before being reacted in solution to produce the polymers.

Cellulose and Cellulose Derivatives

In an embodiment, the polysaccharides are celluloses and/or their derivatives such as carboxymethyl cellulose (CMC), hydroxethyl cellulose (HEC), carboxymethyl hydroxethyl cellulose (CMHEC), hydroxypropyl cellulose, sulfoethyl cellulose and its derivatives, ethyl hydroxyethyl cellulose (EHEC), methyl ethyl hydroxyethyl cellulose (MEHEC), and hydrophobically modified ethyl hydroxyethyl celluloses HM-EHEC some of which are available from AkzoNobel. Polysaccharides also include cellulosic derivatives, including plant heteropolysaccharides commonly known as hemicelluloses which are by-products of the paper and pulp industry. Hemicelluloses include xylans, glucuronoxylans, arabinoxylans, glucomannans, and xyloglucans. Xylans are the most common heteropolysaccharide and are preferred. Polysaccharides such as degradation products of cellulose such as cellobiose are suitable for preparing the polymers as disclosed herein. Polysaccharides also include inulin and its derivatives, such as carboxymethyl inulin. In an embodiment, the preferred cellulosic materials are carboxymethyl cellulose (CMC), hydroxethyl cellulose (HEC), carboxymethyl hydroxethyl cellulose (CMHEC), hydroxypropyl cellulose, ethyl hydroxyethyl cellulose (EHEC), methyl ethyl hydroxyethyl cellulose (MEHEC), and hydrophobically modified ethyl hydroxy ethyl celluloses (HM-EHEC).

Gums

Suitable polysaccharides include guar, unwashed guar gum, washed guar gum, cationic guar, carboxymethyl guar (CM guar), hydroxyethyl guar (HE guar), hydroxypropyl guar (HP guar), carboxymethylhydroxypropyl guar (CMHP guar), hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar), hydrophobically modified cationic guar (HM cationic guar), guar hydroxypropyl triammonium chloride, hydroxypropyl guar hydroxypropyl triammonium chloride.

Polyvinyl Acetate Derivatives

Suitable polyvinyl acetate and derivatives thereof include polyvinyl alcohol, copolymers of polyvinyl alcohol/polyvinyl acetate and copolymers of vinyl acetate and graft copolymers of polyvinyl alcohol/polyvinyl acetate, and polyvinyl pyrollidones. The derivatives of polyvinyl acetate can be anionic such as copolymers with anionic ethylenically unsaturated monomers or non-ionic such as copolymers with non-ionic ethylenically unsaturated monomers.

The polyvinyl acetate derivatives may be completely or partially saponified and/or modified polyvinyl alcohols with a degree of hydrolysis of preferably approximately 70 to 100 mol %, in particular approximately 80 to 98 mol %, and a Hoppler viscosity in 4% aqueous solution of preferably 1 to 50 mPas, in particular of approximately 3 to 40 mPas (measured at 20° C. according to DIN 53015). The weight average molecular weight of the polyvinyl acetate based polymers can be about 1,000,000 or less or 500,000 or less, or about 100,000 or less if it is reacted to form the dried emulsion rheology modifier. The weight average molecular weight of the polyvinyl acetate based polymers can be about 100,000 or less, or about 50,000 or less, or about 10,000 or less.

In one embodiment of the invention the protective water soluble polymers are selected from polyvinyl pyrrolidone and derivatives. The preferred polyvinyl pyrrolidones are homopolymers but copolymers may be used. When a polyvinyl pyrrolidone is used, the polymer may have any molecular weight as long as the rheology modifer remains effective. For example, when polyvinylpyrrolidone is used, it may be specifically PVP K-15 (10,000 in average molecular weight), K-30 (40,000 in average molecular weight), or K-90 (360,000 in average molecular weight) manufactured by Ashland.

Weight average molecular weight of spray drying adjuvant polymers that are starches can be determined by the following procedure:

Starch samples were prepared at 2.00 mg/ml in 0.03M NaCl in dimethylsulfoxide (DMSO). The starch sample solutions were heated at 100° C. for 60 minutes and were clear after heating. The solutions were filtered using a 0.45 micron filter. The molecular weight was measured using gel permeation chromatography with multi-angle light scattering ("GPC/MALS") detection as follows:

| Column | Phenogel Linear 2 30 cm × 7.8 mm |
|---|---|
| Temperature | 60° C. |
| Solvent | 0.03M NaCl in DMSO |
| Flow Rate | 0.60 ml/min |
| Detection | Wyatt Heleos 18 angle MALS and Optilab Rex Refractive Index |

Dried rheology modifier compositions disclosed herein may comprise an anti-caking agent. Examples of anticaking agents include but are not limited to kaolin, aluminosilicates, silicon oxide, aluminum silicon oxide, calcium carbonate, magnesium carbonate, magnesium sulfate, talc, gypsum, silica and silicates, and mixtures thereof. The particle sizes of the anticaking agents are preferably in the range of from 100 nm to 10 µm. More than one anticaking agent may be used.

When the core-shell rheology modifiers of the present disclosure are dried with a spray drying adjuvant polymer, the core-shell polymers are first prepared as described above and then the spray drying adjuvant polymer is added. The core-shell polymer composition can be diluted before the spray drying adjuvant polymer is added. In one embodiment, an aqueous composition of the spray drying adjuvant polymer is added to the core-shell polymer composition with a suitable amount of mixing. Alternatively, the core-shell polymer composition can be added to an aqueous composition of the spray drying adjuvant polymer. In one embodiment, a dry spray drying adjuvant polymer is added to the core-shell polymer composition with concurrent dilution in water. The weight percent of core-shell in the core-shell composition may be in the range of 5-50% and preferably in the range 10-30%. The solids of the aqueous composition of the spray drying adjuvant polymer may be in the range of 5-50% and preferably in the range 10-30%. The solids of the aqueous blend of the core-shell polymer and the spray drying adjuvant polymer may be in the range of 5-50% and preferably in the range 10-30% and most preferably in the range 15-25%. This blend may be dried as is or may be further diluted if necessary before drying. The preferred drying method is spray drying. However, other methods such as drum drying, tray drying, fluidized bed drying etc. may be used. The spray drying adjuvant polymers as described herein will be suitable for use in any of these alternative drying methods.

Product Formulations

In the following description of product formulations that can be prepared with the rheology modifiers disclosed herein, it is intended that the term "rheology modifier" includes the core-shell polymer either in the form of a liquid or dried to a solid, with or without blended spray drying adjuvant polymer, unless otherwise stated.

Product formulations comprising the rheology modifier compositions as disclosed herein may be selected from personal care products, home care products, healthcare products, institutional and industrial care products, adhesives, coatings, agricultural, and formulations for use in electronics industries, and formulations for use in construction industries and other applications. The present application further relates to the use of the rheology modifier compositions as disclosed herein as components of such product formulations along with product formulation active ingredients.

The term "home care products" as used herein includes, without being limited thereto, products employed in a domestic household for surface cleaning or maintaining sanitary conditions, such as in the kitchen and bathroom (e.g., hard surface cleaners, furniture polishes, hand and automatic dish washing formulations, toilet bowl cleaners and disinfectants), and laundry products for fabric care and cleaning (e.g., detergents, fabric conditioners, pre-treatment stain removers), and the like.

The term "health care products" as used herein includes, without being limited thereto, pharmaceuticals (controlled release pharmaceuticals), pharmacosmetics, oral care (mouth and teeth) products, such as oral suspensions, mouthwashes, toothpastes, dentifrices, and the like, and over-the-counter products and appliances (topical and transdermal), such as patches, plasters and the like, externally applied to the body, including the skin, scalp, nails and mucous membranes of humans and animals, for ameliorating a health-related or medical condition, for generally maintaining hygiene or well-being, and the like.

The term "institutional and industrial care" ("I&I") as used herein includes, without being limited thereto, products employed for surface cleaning or maintaining sanitary conditions in institutional and industrial environments, textile treatments (e.g., textile conditioners, carpet and upholstery cleaners), automobile care (e.g., hand and automatic car wash detergents, tire shines, leather conditioners, liquid car polishes, plastic polishes and conditioners), paints and coatings, and the like.

In agricultural applications, the disclosed rheology modifier compositions are useful in agrochemical formulations. They can provide stabilization, thickening, dispersion, or suspension properties to the agrochemical formulations due to their rheological properties. One particularly useful agrochemical formulation is a suspension concentrate (SC). Another particularly useful agrochemical formulation is a solid formulation including wettable powder (WP), water dispersible granule (WDG), and water soluble granule (WSG). When an agrochemical formulation comprising the disclosed rheology modifier compositions is diluted into water, the disclosed rheology modifier compositions can stabilize or suspend agrochemicals in diluted aqueous systems.

In oil field applications, the disclosed rheology modifier compositions can be used in formulations used in fracturing operations. In some applications, it is desired to use liquid compositions with viscoelastic properties. Such compositions, for instance, may be used to stimulate oil wells wherein impeded flow paths lead to an insufficient hydrocarbon production, a technique known as (hydraulic) fracturing and the specialized fluids used in said technique are referred to as fracturing fluids. For such a fracturing process, the compositions are typically injected via the wellbore into the formation at sufficient pressures to create fractures in the formation rocks, thus creating channels through which the hydrocarbons may more readily flow into the wellbore. In an embodiment, the fracturing fluids should impart a minimal pressure drop in the pipe within the wellbore during placement and have an adequate viscosity to carry proppant (sand) material that prevents the fracture from closing. Moreover, the fracturing fluids should have a minimal leak-off rate to avoid fluid migration into the formation rocks so that, notably, the fracture can be created and propagated and should degrade so as not to leave residual material that may prevent accurate hydrocarbons to flow into the wellbore.

Other formulations in which the disclosed rheology modifiers can be used include adhesives, asphalt emulsions, paints and coatings, superabsorbents and other industrial applications.

In an embodiment, the rheology modifiers compositions may be added to these formulations at least about 0.1% modifier by weight of the formulation, more preferably at least about 0.5% modifier by weight of the formulation and most preferably at least about 1.0% modifier by weight of the formulation. The rheology modifiers compositions may be added to these formulations at most about 20% modifier by weight of the formulation, more preferably at most about 15% modifier by weight of the formulation and most preferably at most about 10% modifier by weight of the formulation.

The rheology modifiers can be used in aqueous protective coating compositions. These rheology modifiers increase and maintain the viscosity at required levels under specific processing conditions and end-use situations. In particular, the rheology modifiers are useful in all kinds of coatings such as decorative and protective coatings. The rheology modifiers can be used as rheology modifiers for water-based protective coating compositions. Water-based protective coating compositions are commonly known as latex paints or dispersion paints and have been known for a considerable number of years. The adjustment of the rheology properties of such an aqueous protective coating composition is challenging, since the coating composition must provide good leveling and excellent sag resistance, yet also have a viscosity which is neither too low nor too high in order to allow an easy application.

The polymers as disclosed herein can be used in paper coating applications. A paper coating formulation imparts certain qualities to the paper, including weight, surface gloss, smoothness or reduced ink absorbency. A uniform coating on paper contributes to an enhanced printing surface and properties such as coverage, smoothness, and gloss may be improved. Paper and board grades are sometimes coated to improve the printability, visual properties, or functionality of the sheet. The properties and printability of coated papers are affected by the base sheets (fiber types, sheet formation, internal sizing, and base weight), coating materials (pigment types, binder types, rheology modifiers, water-retention aids, lubricants, defoamers, etc.), coating formulations (ratios of coating components, solids and pH's), coating process (coating application types and speed), coat weights, drying conditions (dryer types, drying temperature, drying time, and final moisture level), etc.

Paper coating formulas typically contain three main categories of ingredients: pigments, binders and additives. Pigments improve printing and optical properties of the sheet, binders adhere the pigment particles to each other and to the sheet, and additives either assist in the coating process or enhance sheet properties. Among the key additives used in paper coating formulations are rheology modifiers. Rheology modifiers are used to achieve desired rheological properties as well as improved runnability during the coating process.

The rheology modifier compositions disclosed herein uncoil when neutralized in the coating formulation, which increases the viscosity. This viscosity increase helps control pick up rates on applicator rolls, affects flow properties during metering processes and changes immobilization and leveling properties after the metering step in the coating process. The ratio of the hydrophilic to hydrophobic monomers in the polymer affects water retention properties and the degree of interaction with the binder. The molecular weight of the polymer and its branching affect both the low shear and high shear viscosity profile.

The rheology modifier compositions which contain a hydrophobically modified alkali swellable polymer are also useful in paper coating applications. Such products are highly effective in lightweight coatings (LWC). These products are used in high solids carbonate coatings, which require water retention with minimal high shear viscosity development.

The term "personal care products" as used herein includes without limitation cosmetics, toiletries, cosmeceuticals, beauty aids, insect repellents, personal hygiene and cleansing products applied to the body, including the skin, hair, scalp, and nails of humans and animals. The personal care applications include, but are not limited to, formulations for hair styling gels, skin creams, sun tan lotions, sunscreens, moisturizers, tooth pastes, medical and first aid ointments, cosmetic ointments, suppositories, cleansers, lipstick, mascara, hair dye, cream rinse, shampoos, body soap and deodorants, hair care and styling formulations, shaving preparations, depilatories and hand sanitizers, including alcohol based hand sanitizers.

Suitable personal care applications also include formulations for use on the skin, eyelashes or eyebrows, including, without limitation, cosmetic compositions such as mascara, facial foundations, eyeliners, lipsticks, and color products; skin care compositions such as moisturizing lotions and creams, skin treatment products, skin protection products in the form of an emulsion, liquid, stick, or a gel; sun care compositions such as sunscreens, sunscreen emulsions, lotions, creams, sunscreen emulsion sprays, liquid/alcohol sunscreen sprays, sunscreen aqueous gels, broad spectrum sunscreens with UVA and UVB actives, sunscreens with organic and inorganic actives, sunscreens with combinations of organic and inorganic actives, suntan products, self-tanning products, and after sun products etc. Particularly suitable compositions are personal care emulsions, more particularly suitable are sun care compositions such as sunscreen emulsions and sunscreen emulsion sprays. The personal care composition may be in any form, including without limitation in sprays, emulsions, lotions, gels, liquids, sticks, waxes, pastes, powders, and creams.

The personal care compositions may also include other optional components commonly used in the industry, and these will vary greatly depending upon the type of composition and the functionality and properties desired. Without limitation, these components include thickeners, suspending agents, emulsifiers, UV filters, sunscreen actives, humectants, moisturizers, emollients, oils, waxes, solvents, chelating agents, vitamins, antioxidants, botanical extracts, silicones, neutralizing agents, preservatives, fragrances, dyes, pigments, conditioners, polymers, antiperspirant active ingredients, antiacne agents, anti-dandruff actives, surfactants, exfoliants, depilatory active ingredients, film formers, propellants, tanning accelerator, hair fixatives and colors. The polymers are compatible with most other components used in conventional personal care compositions. For example, sunscreen compositions may contain at least one component selected from the group comprising organic UV filters, inorganic UV actives, UVA and/or UVB sunscreen actives, octinoxate, octisalate, oxybenzone, homosalate, octocrylene, avobenzene, titanium dioxide, starch, conditioning agents, emulsifiers, other rheology modifiers and thickeners, neutralizers, emollients, solvents, film formers, moisturizers, antioxidants, vitamins, chelating agents, preservatives, fragrances, and zinc oxide. Skin care and cosmetic compositions may contain at least one component selected from the group consisting of vitamins, anti-aging agents, moisturizers, emollients, emulsifiers, surfactants, preservatives, pigments, dyes, colors and insect repellents.

When used in personal care formulations, such as hair care and styling formulations, for example styling gels, optional additional ingredients can be added to provide a variety of further additional properties. Various other additives, such as active and functional ingredients, may be included in the personal care formulation as defined herein. These include, but are not limited to, emollients, humectants, thickening agents, electrolytes and salts surfactants, UV light inhibitors, fixative polymers preservatives pigments dyes, colorants, alpha hydroxy acids, aesthetic enhancers such as starch perfumes and fragrances, film formers (water proofing agents) antiseptics, antifungal, antimicrobial and other medicaments and solvents. Additionally, conditioning agents can be used in combination with the disclosed polymers, for example, cationic guar gum, cationic hydroxyethyl cellulose, cationic synthetic polymers and cationic fatty amine derivatives. These blended materials help to provide more substantivity and effective conditioning properties in hair. The electrolytes and salts are particularly useful in boosting the viscosity of the shampoo and improving its suspending properties.

The personal care, home care, health care and I&I care compositions comprising the staged core-shell polymers can be formulated at pH ranges from about 0.5 to about 12. The desired pH for the compositions is obviously dependent upon the specific end product applications. Generally, personal care applications have a pH range of about 3 to about 10 in one aspect, and from about 4.5 to about 10 in another aspect. In another aspect, the staged core-shell polymer/surfactant compositions when formulated at pH values of about 6 and below give a clear formulation while maintaining desirable rheology properties of the compositions in which they are included. In still another aspect, the staged core-shell/surfactant compositions when formulated at pH values of about 5.0 and below give a clear formulation while maintaining desirable rheology properties of the compositions in which they are included.

Generally, home care applications have a desired pH range of about 1 to about 12 in one aspect, and from about 3 to about 10 in another aspect, depending on the desired end-use application.

The pH of the compositions as disclosed herein can be adjusted with any combination of acidic and/or basic pH adjusting agents known to the art.

An alkaline material is incorporated to neutralize the polymer and can be referred to as a neutralizing agent or pH adjusting agent. Many types of neutralizing agents can be used, including inorganic and organic bases, and combinations thereof. Examples of inorganic bases include but are not limited to the alkali metal hydroxides (especially sodium, potassium, and ammonium), and alkali metal salts of inorganic acids, such as sodium borate (borax), sodium phosphate, sodium pyrophosphate, and the like; and mixtures thereof. Examples of organic bases include but are not limited to triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, 2-amino 2-hydroxymethyl-1,3-propanediol, and PEG-15 cocamine. Alternatively, other alkaline materials can be used alone or in combination with the above mentioned inorganic and organic bases. Such materials include surfactants, surfactant mixtures, pre-neutralized surfactants or materials that when combined in a composition containing the staged core-shell polymer is capable of neutralizing or partially neutralizing the carboxyl groups on the staged core-shell polymer backbone. Any material capable of increasing the pH of the composition is suitable.

Various acidic materials can be utilized as a pH adjusting agent. Such acidic materials include organic acids and inorganic acids, for example, acetic acid, citric acid, tartaric acid, alpha-hydroxy acids, beta-hydroxy acids, salicylic acid, lactic acid, glycolic acid, and natural fruit acids, or inorganic acids, for example, hydrochloric acid, nitric acid, sulfuric acid, sulfamic acid, phosphoric acid, and combinations thereof. As discussed above, the addition of the acidic pH adjusting agent can be incorporated after the addition of the basic pH adjusting agent in a desired composition.

As with the alkaline pH adjusting agents, other acidic materials can be used alone or in combination with the above mentioned inorganic and organic acids. Such materials include materials which when combined in a composition containing the staged core-shell polymer are capable of reducing the pH of the composition. It will be recognized by the skilled artisan that the acidic pH adjusting agents can serve more than one function. For example, acidic preservative compounds and acid based cosmeceutical compounds (e.g., alpha- and beta-hydroxy acids) not only serve their primary preservative and cosmeceutical functions, respectively, they can also be utilized to reduce or maintain the pH of a desired formulation.

Buffering agents can be used in the disclosed compositions. Suitable buffering agents include, but are not limited to, alkali or alkali earth metal carbonates, phosphates, bicarbonates, citrates, borates, acetates, acid anhydrides, succinates, and the like, such as sodium phosphate, sodium citrate, sodium acetate, sodium bicarbonate, and sodium carbonate.

The pH adjusting agent and/or buffering agent is utilized in any amount necessary to obtain and/or maintain a desired pH value in the composition.

The core-shell polymers disclosed herein can be formulated with or without at least one surfactant. Such compositions can comprise any combination of optional additives, adjuvants, and benefit agents suitable for a desired personal care, home care, health care, and institutional and industrial care product known in the art. The choice and amount of each optional component employed will vary with the purpose and character of the end product, and can be readily determined by one skilled in the formulation art and from the literature. It is recognized that various additive, adjuvant, and benefit agents and components set forth herein can serve more than one function in a composition, such as, for example, surfactants, emulsifiers, solubilizers, conditioners, emollients, humectants, lubricants, pH adjusting agents, and acid based preservatives.

While overlapping weight ranges for the various components and ingredients that can be contained in the compositions have been expressed for selected embodiments and aspects as disclosed herein, it should be readily apparent that the specific amount of each component in the disclosed personal care, home care, health care, and I&I care compositions will be selected from its disclosed range such that the amount of each component is adjusted such that the sum of all components in the composition will total 100 weight percent The amounts employed will vary with the purpose and character of the desired product and can be readily determined by one skilled in the formulation art and from the literature.

Optional additives and adjuvants include, but are not limited to insoluble materials, pharmaceutical and cosmeceutical actives, chelators, conditioners, diluents, solvents, fragrances, humectants, lubricants, solubilizers, emollients, opacifiers, colorants, anti-dandruff agents, preservatives, spreading aids, emulsifiers, sunscreens, fixative polymers, botanicals, viscosity modifiers, and the like, as well as the numerous other optional components for enhancing and maintaining the properties of a desired personal care, home care, health care, and I&I care composition.

In an embodiment, the rheology modifier has to be neutralized with an alkali to the pH of 6-6.5 and above to be activated. However, it is desirable to have some formulations, especially personal care formulations, in the pH range 4 to 5.5. For such formulations, the rheology modifier composition containing the alkali swellable polymers can be mixed into an aqueous formulation containing surfactants, activated by neutralization to a pH of about 6.5 or higher and subsequently acidified in the presence of a surfactant to lower the formulation pH to 3-6.5, preferably to 4-5.5 in accordance with the back acid titration process described in U.S. Pat. Nos. 4,529,773, 6,635,702 and 6,897,253, the disclosures of each of which are incorporated herein by reference in their entireties.

Some non-limiting examples of polymers that can used in personal care formulations in conjunction with the rheology modifier compositions disclosed herein are polyoxythylenated vinyl acetate/crotonic acid copolymers, vinyl acetate crotonic acid (90/10) copolymers, vinyl acetate/crotonic acid/vinyl neodecanoate terpolymers, N-octylacrylamide/ methylacrylate/hydroxypropyl methacrylate/acrylic acid/ tert-butylaminoethyl methacrylate copolymers, and methyl vinyl ether/maleic anhydride (50/50) copolymers monoesterified with butanol or ethanol, acrylic acid/ethyl acrylate/ N-tert-butyl-acrylamide terpolymers, and poly (methacrylic acid/acrylamidomethyl propane sulfonic acid), acrylates copolymer, octylacrylamide/acrylates/butylaminoethyl methacrylate copolymer, acrylates/octylacrylamide copolymer, VA/crotonates/vinyl Neodeanoate copolymer, poly(N-vinyl acetamide), poly(N-vinyl formamide), corn starch modified, sodium polystyrene sulfonate, polyquaterniums such as polyquaternium-4, polyquaternium-7, polyquaternium-10, polyquaternium-11, polyquarternium-16, polyquaternium-28, polyquaternium-29, polyquaternium-46, polyether-1, polyurethanes, VA/acrylates/lauryl methacrylate copolymer, adipic acid/dimethylaminohydroxypropyl diethylene AMP/acrylates copolymer, methacrylol ethyl betaine/acrylates copolymer, PVP/dimethylaminoethyl-methacrylate copolymer, PVP/DMAPA acrylates copolymer, PVP/vinylcaprolactam/DMAPA acrylates copolymer, vinyl caprolactam/PVP/dimethylaminoethyl methacrylate copolymer, VA/butyl maleate/isobornyl acrylate copolymer, VA/crotonates copolymer, acrylate/acrylamide copolymer, VA/crotonates/vinyl propionate copolymer, vinylpyrrolidone/vinyl acetate/vinyl propionate terpolymers, VA/crotonates, cationic and amphoteric guar, polyvinylpyrrolidone (PVP), polyvinylpyrrolidone/vinyl acetate copolymer, PVP acrylates copolymer, vinyl acetate/crotonic acid/vinyl proprionate, acrylates/acrylamide, acrylates/octylacrylamide, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate and isobornyl acrylate copolymer, vinylcaprolactam/PVP/dimethylaminoethyl methacrylate, vinyl acetate/alkylmaleate half ester/N-substituted acrylamide terpolymers, vinyl caprolactam/vinylpyrrolidone/methacryloamidopropyl trimethylammonium chloride terpolymer methacrylates/acrylates copolymer/amine salt, polyvinylcaprolactam, polyurethanes, hydroxypropyl guar, hydroxypropyl guar hydroxypropyl trimmonium chloride, poly (methacrylic acid/acrylamidomethyl propane sulfonic acid, poylurethane/acrylate copolymers and hydroxypropyl trimmonium chloride guar, particularly acrylates copolymer, octylacrylamide/acrylates/butylaminoethyl methacrylate copolymer, acrylates/octylacrylamide copolymer, VA/crotonates/vinyl Neodecanoate copolymer, poly(N-vinyl acetamide), poly(N-vinyl formamide), polyurethane, corn starch modified, sodium polystyrene sulfonate, polyquaternium-4, polyquarternium-10, and polyurethane/acrylates copolymer.

Suitable cationic polymers that may be used in formulations comprising the disclosed rheology modifier compositions are those best known with their CTFA category name Polyquaternium. Some examples of this class of polymer are Polyquaternium 6, Polyquaternium 7, Polyquaternium 10, Polyquaternium 11, Polyquaternium 16, Polyquaternium 22 and Polyquaternium 28, Polyquaternium 4, Polyquaternium 37, Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

Naturally derived cellulose type polymers known as Polymer JR® type from Amerchol, Polyquaternium 10 or cationic guar gum known with trade name Jaguar® from Rhone-Poulenc, and Guar hydroxypropyl trimonium chloride, chitosan and chitin can also be included in the personal care formulations as cationic natural polymers in formulations comprising the disclosed rheology modifier compositions.

The rheology modifiers may be used in personal care compositions that may also include a cosmetically acceptable ingredient. The ingredient can be an emollient, fragrance, exfoliant, medicament, whitening agent, acne treatment agent, a preservative, vitamins, proteins, a cleanser or conditioning agent.

Examples of cleansers suitable for use in compositions herein include, but are not limited to, are sodium lauryl sulfate (SLS), sodium laureth sulfate (SLES), ammonium lauryl ether sulfate (ALES), alkanolamides, alkylaryl sulfonates, alkylaryl sulfonic acids, amine oxides, alkylbenzyl acetates, amines, sulfonated amines and amides, betaines, block polymers, carboxylated alcohol or alkylphenol ethoxylates, diphenyl sulfonate derivatives, ethoxylated alcohols, ethoxylated alkylphenols, ethoxylated amines and/or amides, ethoxylated fatty acids, ethoxylated fatty esters and oils, fatty esters (other than glycol, glycerol, etc.), fluorocarbon-based surfactants, glycerol esters, glycol esters, heterocyclics, imidazolines and imidazoline derivatives, isethionates, lanolin-based derivatives, lecithin and lecithin derivatives, lignin and lignin derivatives, methyl esters, monoglycerides and derivatives, olefin sulfonates, phosphate esters, phosphorous organic derivatives, polymeric (polysaccharides, acrylic acid, acrylamide), propoxylated and ethoxylated fatty acids, propoxylated and ethoxylated fatty alcohols, propoxylated and ethoxylated alkyl phenols, protein-based surfactants, quaternary surfactants, sarcosine derivatives, silicone-based surfactants, soaps, sorbitan derivative, sucrose and glucose esters and derivatives, sulfates and sulfonates of oils and fatty acids, sulfates and sulfonates ethoxylated alkyl phenols, sulfates of alcohols, sulfates of ethoxylated alcohols, sulfates of fatty esters, sulfonates of benzene, cumene, toluene and xylene, sulfonates of condensed naphthalenes, sulfonates of dodecyl and tridecyl benzenes, sulfonates of naphthalene and alkyl naphthalene, sulfonates of petroleum, sulfosuccinamates, sulfosuccinates and derivatives.

In other embodiments, the personal care formulation comprising the disclosed rheology modifier is a hair fixative or styling formulation, such as a hair gel, mousse, spray, pomade, wax, or styling lotion. Surprisingly, it has been found that some embodiments of rheology modifiers disclosed herein can be formulated into such hair fixative and styling formulations, to produce not only desired rheology modification, but also hair holding properties. When the disclosed rheology modifiers are used in such formulations, it is possible to reduce or even eliminate other additives that have traditionally been used to provide these functions.

In addition to the polymer(s) disclosed herein, personal care compositions may optionally include other ingredients. Some non-limiting examples of these ingredients include, but are not limited to, conditioning agents such as silicone oils, either volatile or non-volatile, natural and synthetic oils. Suitable silicone oils that can be added to the compositions include dimethicone, dimethiconol, polydimethylsiloxane, silicone oils with various DC fluid ranges from Dow Corning. Suitable natural oils, such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate can also be used. Some examples of non-ionic conditioning agents are polyols such as glycerin, glycol and derivatives, polyethyleneglycols, which may be known by the trade names Carbowax® PEG from Union Carbide and Polyox® WSR range from Amerchol, polyglycerin, polyethyleneglycol mono- or di-fatty acid esters.

Preservatives can be used in personal care formulations to provide long term shelf stability. These can be selected from among methylparaben, propylparaben, butylparaben, DMDM hydantoin, imidazolidinyl urea, gluteraldehyde, phenoxyethanol, benzalkonium chloride, methane ammonium chloride, benzethonium chloride, benzyl alcohol, chlorobenzyl alcohol, methylchloroisothiazolinone, methylisothiazolinone, sodium benzoate, chloracetamide, triclosan, iodopropynyl butylcarbamate, sodium pyrithione, and zinc pyrithione.

The rheology modifier compositions as disclosed herein can also be used in liquid detergent compositions that include one or more surfactants, such as those selected from anionic, nonionic, cationic, amphoteric, and zwitterionic surfactants. In an embodiment, the preferred surfactants are suitable for use in isotropic liquid detergent compositions and are mixtures of anionic and nonionic surfactants although it is to be understood that any surfactant may be used alone or in combination with any other surfactant or surfactants. These liquid detergent systems as well as the surfactants used in them are described in U.S. Pat. No. 6,462,013 which is incorporated herein by reference in its entirety.

Liquid detergent compositions comprising the disclosed rheology modifier compositions may also be used in liquid detergent compositions and may further optionally comprise at least one additive. Suitable additives may include, for example, builders, dispersants, polymers, ion exchangers, alkalis, anticorrosion materials, antiredeposition materials, antistatic agents, optical brighteners, perfumes, fragrances, dyes, fillers, oils, chelating agents, enzymes, fabric whiteners, brighteners, sudsing control agents, solvents, hydrotropes, bleaching agents, bleach precursors, buffering agents, soil removal agents, soil release agents, fabric softening agents, and opacifiers. In general, such additives and their amounts are known to those skilled in the art.

Formulation Surfactants

In one aspect, stable aqueous formulations comprise a staged core-shell rheology modifier as disclosed herein and a surfactant(s). Suitable surfactants include anionic, cationic, amphoteric, and nonionic surfactants, as well as mixtures thereof. Such compositions are useful, for example, in personal care cleansing compositions that contain various components such as substantially insoluble materials requiring suspension or stabilization (e.g., a silicone, an oily material, a pearlescent material, aesthetic and cosmeceutical beads and particles, gaseous bubbles, exfoliants, and the like).

The anionic surfactant can be any of the anionic surfactants known or previously used in the art of aqueous surfactant compositions. Suitable anionic surfactants include but are not limited to alkyl sulfates, alkyl ether sulfates, alkyl sulfonates, alkaryl sulfonates, $\alpha$-olefin-sulphonates, alkylamide sulfonates, alkarylpolyether sulfates, alkylamidoether sulfates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulfoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants contain from about 6 to about 24 carbon atoms in one aspect, from 8 to 22 carbon atoms in another aspect and from about 12 to 18 carbon atoms in a further aspect and may be unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, ammonium, and triethanolamine lauryl sulfate, coco sulfate, tridecyl sulfate, myrstyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcocinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from about 8 to about 22 carbon atoms.

The cationic surfactants can be any of the cationic surfactants known or previously used in the art of aqueous surfactant compositions. Suitable classes of cationic surfactants include but are not limited to alkyl amines, alkyl imidazolines, ethoxylated amines, quaternary compounds, and quaternized esters. In addition, alkyl amine oxides can function as a cationic surfactant at a low pH.

Alkylamine surfactants can be salts of primary, secondary and tertiary fatty $C_{12}$-$C_{22}$ alkylamines, substituted or unsubstituted, and substances sometimes referred to as "amidoamines". Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane).

Non-limiting examples of amidoamines and salts thereof include stearamido propyl dimethyl amine, stearamidopropyl dimethylamine citrate, palmitamidopropyl diethylamine, and cocamidopropyl dimethylamine lactate.

Non-limiting examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Non-limiting examples of ethyoxylated amines include PEG-cocopolyamine, PEG-15 tallow amine, quaternium-52, and the like.

Among the quaternary ammonium compounds useful as cationic surfactants, some correspond to the general formula: $(R^5R^6R^7R^8N^+)$ $E^-$, wherein $R^5$, $R^6$, $R^7$, and W are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g., chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated. In one aspect, the aryl groups are selected from phenyl and benzyl.

Exemplary quaternary ammonium surfactants include, but are not limited to cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride, benzalkonium chloride, benzethonium chloride, and di(coconutalkyl)dimethyl ammonium chloride, ditallowedimethyl ammonium chloride, di(hydrogenated tallow)dimethyl ammonium chloride, di(hydrogenated tallow)dimethyl ammonium acetate, ditallowedimethyl ammonium methyl sulfate, ditallow dipropyl ammonium phosphate, and ditallow dimethyl ammonium nitrate.

Examples of suitable amine oxide surfactants include, but are not limited to, dimethyl-dodecylamine oxide, oleyldi(2-hydroxyethyl)amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

Amphoteric or zwitterionic surfactants are molecules that contain acidic and basic moieties and have the capacity of behaving either as an acid or a base. Suitable surfactants can be any of the amphoteric surfactants known or previously used in the art of aqueous surfactant compositions. Exemplary amphoteric surfactant classes include but are not limited to amino acids (e.g., N-alkyl amino acids and N-acyl amino acids), betaines, sultaines, and alkyl amphocarboxylates.

Suitable amino acid based surfactants include surfactants represented by the formula:

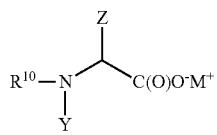

wherein $R^{10}$ represents a saturated or unsaturated hydrocarbon group having 10 to 22 carbon atoms or an acyl group containing a saturated or unsaturated hydrocarbon group having 9 to 22 carbon atoms, Y is hydrogen or methyl, Z is selected from hydrogen, —$CH_3$, —$CH(CH_3)_2$, —$CH_2CH(CH_3)_2$, —$CH(CH_3)CH_2CH_3$, —$CH_2C_6H_5$, —$CH_2C_6H_4OH$, —$CH_2OH$, —$CH(OH)CH_3$, —$(CH_2)_4NH_2$, —$(CH_2)_3NHC(NH)NH_2$, —$CH_2C(O)O^-M^+$, —$(CH_2)_2C(O)O^-M^+$. M is a salt forming cation. In one aspect, $R^{10}$ represents a radical selected from a linear or branched $C_{10}$ to $C_{22}$ alkyl group, a linear or branched $C_{10}$ to $C_{22}$ alkenyl group, an acyl group represented by $R^{11}C(O)$—, wherein $R^{11}$ is selected from a linear or branched $C_9$ to $C_{22}$ alkyl group, a linear or branched $C_9$ to $C_{22}$ alkenyl group. In one aspect, $M^+$ is selected from sodium, potassium, ammonium, and triethanolamine (TEA).

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants are, but not limited to the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

The betaines and sultaines useful in the disclosed compositions are selected from alkyl betaines, alkylamino betaines, and alkylamido betaines, as well as the corresponding sulfobetaines (sultaines) represented by the formulas:

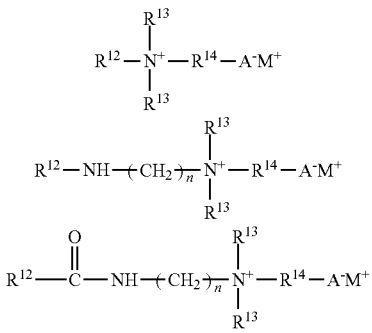

wherein $R^{12}$ is a $C_7$-$C_{22}$ alkyl or alkenyl group, each $R^{13}$ independently is a $C_1$-$C_4$ alkyl group, $R^{14}$ is a $C_1$-$C_5$ alkylene group or a hydroxy substituted $C_1$-$C_5$ alkylene group, n is an integer from 2 to 6, A is a carboxylate or sulfonate group, and M is a salt forming cation. In one aspect, $R^{12}$ is a $C_{11}$-$C_{18}$ alkyl group or a $C_{11}$-$C_{18}$ alkenyl group. In one aspect, $R^{13}$ is methyl. In one aspect, $R^{14}$ is methylene, ethylene or hydroxy propylene. In one aspect, n is 3. In a further aspect, M is selected from sodium, potassium, magnesium, ammonium, and mono-, di- and triethanolamine cations.

Examples of suitable betaines include, but are not limited to, lauryl betaine, coco betaine, oleyl betaine, cocohexadecyl dimethylbetaine, lauryl amidopropyl betaine, oleamidopropyl betaine, cocoamidopropyl betaine, and cocamidopropyl hydroxysultaine.

The alkylamphocarboxylates such as the alkylamphoacetates and alkylamphopropionates (mono- and disubstituted carboxylates) can be represented by the formula:

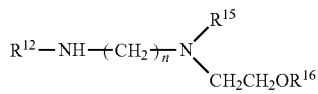

wherein $R^{12}$ is a $C_7$-$C_{22}$ alkyl or alkenyl group, $R^{15}$ is —$CH_2C(O)O^-M^+$, —$CH_2CH_2C(O)O^-M^+$, or —$CH_2CH(OH)CH_2SO_3^-M^+$, $R^{16}$ is a hydrogen or —$CH_2C(O)O^-M^+$, and M is a cation selected from sodium, potassium, magnesium, ammonium, and mono-, di- and triethanolamine.

Exemplary alkylamphocarboxylates include, but are not limited to, sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

The nonionic surfactant can be any of the nonionic surfactants known or previously used in the art of aqueous surfactant compositions. Suitable nonionic surfactants include, but are not limited to, aliphatic ($C_6$-$C_{18}$) primary or secondary linear or branched chain acids, alcohols or phenols; alkyl ethoxylates; alkyl phenol alkoxylates (especially ethoxylates and mixed ethoxy/propoxy moieties); block alkylene oxide condensates of alkyl phenols; alkylene oxide condensates of alkanols; and ethylene oxide/propylene oxide block copolymers. Other suitable nonionic surfactants include mono- or dialkyl alkanolamides; alkyl polyglucosides (APGs); sorbitan fatty acid esters; polyoxyethylene sorbitan fatty acid esters; polyoxyethylene sorbitol esters; polyoxyethylene acids, and polyoxyethylene alcohols. Other examples of suitable nonionic surfactants include coco mono- or diethanolamide, coco glucoside, decyl diglucoside, lauryl diglucoside, coco diglucoside, polysorbate 20, 40, 60, and 80, ethoxylated linear alcohols, cetearyl alcohol, lanolin alcohol, stearic acid, glyceryl stearate, PEG-100 stearate, laureth 7, and oleth 20.

In another embodiment, non-ionic surfactants include, but are not limited to, alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357, the disclosures of which are hereby incorporated by reference in their entirety.

Other surfactants which can be utilized in the disclosed compositions are set forth in more detail in WO 99/21530, U.S. Pat. Nos. 3,929,678, 4,565,647, 5,720,964, and 5,858, 948. In addition, suitable surfactants are also described in *McCutcheon's Emulsifiers and Detergents* (North American and International Editions, by Schwartz, Perry and Berch) which is hereby fully incorporated by reference.

While the amounts of the surfactant utilized in a composition comprising the disclosed staged core-shell polymer can vary widely depending on a desired application, the amounts which are often utilized generally range from about 1% to about 80% by weight in one aspect, from about 3% to about 65% weight in another aspect, from about 5% to about 30% by weight in a still another aspect, from about 6% to about 20% by weight in a further aspect, and from about 8% to about 16% by weight, based upon the total weight of the personal care, home care, health care, and institutional and industrial care composition in which it is included.

In one aspect, the personal care, home care, health care and I&I care compositions disclosed herein comprise a staged core-shell polymer in combination with at least one anionic surfactant. In another aspect, the compositions comprise a staged core-shell polymer with at least one anionic surfactant and at least one amphoteric surfactant. In one aspect, the anionic surfactant is selected from alkyl sulfates, alkyl ether sulfates, alkyl sulphonates, alkaryl sulfonates, alkarylpolyether sulfates, and mixtures thereof wherein the alkyl group contains 10 to 18 carbon atoms, the aryl group is a phenyl, and the ether group contains 1 to 10 moles of ethylene oxide. Representative anionic surfactants include, but are not limited to, sodium and ammonium lauryl ether sulfate (ethoxylated with 1, 2, and 3 moles of ethylene oxide), sodium, ammonium, and triethanolamine lauryl sulfate.

In one aspect, the amphoteric surfactant is selected from an alkyl betaine, an alkylamino betaine, an alkylamido betaines, and mixtures thereof. Representative betaines include but are not limited to lauryl betaine, coco betaine, cocohexadecyl dimethylbetaine, cocoamidopropyl betaine, cocoamidopropylhydroxy sultaine, and mixtures thereof.

In an embodiment, particularly where the formulation is a shampoo or a cleaning formulation such as a body wash, the formulation further comprises a sulfate free surfactant. Examples of sulfate free surfactants include, but are not limited to, ethoxylated alkylphenols, ethoxylated amines and/or amides, ethoxylated fatty acids, ethoxylated fatty esters and oils, fatty esters (other than glycol, glycerol, etc.), fluorocarbon-based surfactants, glycerol esters, glycol esters, heterocyclics, imidazolines and imidazoline derivatives, isethionates, lanolin-based derivatives, lecithin and lecithin derivatives, lignin and lignin derivatives, methyl esters, monoglycerides and derivatives, phosphate esters, phosphorous organic derivatives, polymeric (polysaccharides, acrylic acid, acrylamide), propoxylated and ethoxylated fatty acids, propoxylated and ethoxylated fatty alcohols, propoxylated and ethoxylated alkyl phenols, protein-based surfactants, quaternary surfactants, sarcosine derivatives, siliconebased surfactants, alpha-olefin sulfonate, alkylaryl sulfonates, sulfonates of oils and fatty acids, sulfonates of ethoxylated alkyl phenols, sulfonates of benzene, cumene, toluene and xylene, sulfonates of condensed naphthalenes, sulfonates of dodecyl and tridecyl benzenes, sulfonates of naphthalene and alkyl naphthalene, sulfonates of petroleum and derivatives thereof. In an embodiment, the sulfate free surfactants are sulfonates or ethoxylates.

In another embodiment the formulation contains sulfated surfactants. Some non-limiting examples of sulfated surfactants are sodium lauryl sulfate (SLS), sodium laureth sulfate (SLES), alkanolamides, alkylaryl sulfonic acids, sulfates of oils and fatty acids, sulfates of ethoxylated alkyl phenols, sulfates of alcohols, sulfates of ethoxylated alcohols, sulfates of fatty esters, sulfosuccinamates, sulfosuccinates and derivatives thereof.

EXAMPLES

The following examples are intended to illustrate various embodiments of the disclosed rheology modifiers and formulations containing these rheology modifiers, and are not intended to limit the scope of the claims appended hereto.

In the Examples and accompanying tables, the following materials and abbreviations are used.

BA—n-butyl acrylate available from Arkema, Ala.
EA—ethyl acrylate available from Sasol-Bayonne, NJ
MAA—methacrylic acid available from Evonik-Avondale, LA
MMA—methyl methacrylate available from Lucite-Nederland, TX
BEI—behenyl ethoxylate itaconate of formula I(B) available from AkzoNobel Chemicals, NC
CD559—alkyl ethoxylate methacrylate ester of formula I(A), illustrated above available from AkzoNobel Chemicals, NC
SLS—sodium lauryl sulfate 30% solution available from Royal Coatings and Specialty Polymers, IN
2-ME—2-mercaptoethanol available from Millipore Sigma, MA
TMPTA—trimethylolpropane triacrylate available from Millipore Sigma, MA EGDMA—ethylene glycol dimethacrylate available from Millipore Sigma, MA
DAP—diallyl phthalate available from Millipore Sigma, MA

Examples 1-29—Core-Shell Polymers Prepared Using Monomer Pre-Emulsion

For each of Examples 1-29, a solution of 247 g water and 7.58 g sodium lauryl sulfate 30% solution (SLS) was prepared as the initial charge in a 1 L reactor. The reactor contents were heated to 85° C. with overhead stirring and an overhead nitrogen sparge. A monomer pre-emulsion was prepared in a graduated cylinder with overhead agitation according to the components and gram amounts listed in Table 1A under the heading "Monomer pre-emulsion components" and with molar percentages listed in Table 1C. When the reactor contents had been at temperature for one hour, a small amount of the monomer pre-emulsion was added subsurface to the reactor contents as specified in the "Seed charge" column. The contents were stirred for 15 minutes, at which time an initiator solution containing 0.31 g sodium persulfate dissolved in 17.5 g water was added to the reactor contents. The reactor contents were agitated for another 15 minutes, at which time the remaining monomer pre-emulsion was added subsurface over the time period specified in the column "Core add time". An initiator solution of 0.28 g sodium persulfate in 62.5 g water was also added into the reactor starting at the same time as the core slow add, at a rate of 0.26 g/min. Upon completion of the core feed, a second monomer solution comprising the components and gram amounts listed under the heading "Monomer mixture components" in Table 1B and with molar percentages listed in Table 1D was fed into the reactor over the time period specified in the column "Shell add time". When the shell slow add had completed, the initiator solution addition rate was doubled to 0.52 g/min so that the feed would finish in one hour. When the initiator slow add was complete, the temperature of the reactor contents was raised to 90° C. and the contents were held at that temperature, with stirring, for one additional hour. The reactor contents were cooled to ambient and the product was a white emulsion to which was added 47 g of water.

Examples 30-33—Core-Shell Polymers Prepared Using Initial Quick Addition of Monomer Mixture For each of Examples 30-33, a solution of 247 g water and 7.58 g sodium lauryl sulfate 30% solution surfactant was prepared as the initial charge in a 1 L reactor. The reactor contents were heated to 85° C. with overhead stirring and an overhead nitrogen sparge. A surfactant solution comprising 289.2 g water and 7.58 g sodium laurel sulfate 30% solution was prepared in a graduated cylinder. A monomer mixture was prepared according to the components and gram amounts listed in Table 2A under the heading "Monomer mixture components" and with molar percentages listed in Table 2C in another graduated cylinder. When the reactor contents had been at temperature for one hour, 13.3 g of the monomer mixture and then 14.8 g of the surfactant solution in the graduated cylinder were quickly shot into the reactor. The contents were stirred for 15 minutes, at which time an initiator solution containing 0.31 g sodium persulfate dissolved in 17.5 g water was added to the reactor contents. The reactor contents were agitated for another 15 minutes. At this time, the remaining monomer mixture was added subsurface over the time period specified in the column "Core add time" in Table 2A, and the surfactant solution was added to the reactor contents over a period of 100 minutes. An initiator solution of 0.28 g sodium persulfate in 62.5 g water was also added into the reactor starting at the same time as the core slow add, at a rate of 0.26 g/min. Upon completion of the core feed, a second monomer solution comprising the components and gram amounts listed under the heading "Monomer mixture components" in Table 2B and with mole percentages listed in Table 2D was fed into the reactor over the time period specified in the column "Shell add time". When the shell slow add had completed, the initiator solution addition rate was doubled to 0.52 g/min so that the feed would finish in one hour. When the initiator slow add was complete, the temperature of the reactor contents was raised to 90° C. and the contents were held at that temperature, with stirring, for one additional hour. The reactor contents were cooled to ambient and the product was a white emulsion to which was added 47 g of water.

TABLE 1A

Core stage of Examples 1-29. Gram amounts of components and time over which core stage pre-emulsions were added. 2-ME was added as a 10% solution in water; amounts listed are grams 2-ME.

| Example Number | Water | 30% SLS | MAA | MMA | EA | BA | CD559 | BEI | TMPTA | 2-ME | Seed Charge | Core add time (min) |
|---|---|---|---|---|---|---|---|---|---|---|---|---|
| 1 | 289.2 | 7.58 | 100.61 | 61.6 | 63 | — | 39 | — | — | 0.0874 | 28.1 | 100 |
| 2 | 289.2 | 7.58 | 100.61 | 61.6 | 63 | — | 39 | — | — | 0.0874 | 28.1 | 100 |
| 3 | 289.2 | 7.58 | 100.61 | 61.6 | 63 | — | 39 | — | — | 0.0874 | 28.1 | 100 |
| 4 | 289.2 | 7.58 | 100.61 | 61.6 | 63 | — | 39 | — | — | 0.0874 | 28.1 | 100 |
| 5 | 289.2 | 7.58 | 100.61 | 61.6 | 63 | — | 39 | — | — | 0.0874 | 28.1 | 100 |
| 6 | 289.2 | 7.58 | 100.61 | 61.6 | 63 | — | 39 | — | — | 0.0874 | 28.1 | 100 |
| 7 | 289.2 | 7.58 | 100.61 | 61.6 | 63 | — | 39 | — | — | 0.0874 | 28.1 | 100 |
| 8 | 289.2 | 7.58 | 100.61 | 61.6 | 63 | — | 39 | — | — | 0.0874 | 28.1 | 100 |
| 9 | 289.2 | 7.58 | 100.61 | 61.6 | 63 | — | 39 | — | — | 0.0874 | 28.1 | 100 |
| 10 | 289.2 | 7.58 | 100.61 | 61.6 | 63 | — | 39 | — | — | 0.0874 | 28.1 | 100 |
| 11 | 289.2 | 7.58 | 100.61 | 61.6 | 63 | — | 39 | — | 0.56 | 0.0874 | 28.3 | 100 |
| 12 | 298.9 | 7.58 | 110.36 | 61.6 | 63 | — | — | — | — | — | 27 | 100 |
| 13 | 289.2 | 7.58 | 100.61 | 61.6 | 42 | 21 | 39 | — | — | 0.0874 | 28.3 | 100 |
| 14 | 289.2 | 7.58 | 70.43 | 43.12 | 44.1 | — | 27.3 | — | — | 0.06118 | 36.2 | 70 |
| 15 | 289.2 | 7.58 | 70.43 | 43.12 | 44.1 | — | 27.3 | — | — | 0.06118 | 36.2 | 70 |
| 16 | 298.45 | 7.58 | 110.36 | 61.6 | 63 | — | — | — | — | 0.0874 | 27.1 | 100 |
| 17 | 298.95 | 7.58 | 110.36 | 61.6 | 63 | — | — | — | — | 0.0874 | 27.1 | 100 |
| 18 | 284.3 | 7.58 | 95.73 | 61.6 | 63 | — | 58.5 | — | — | 0.0175 | 28.6 | 100 |

TABLE 1A-continued

Core stage of Examples 1-29. Gram amounts of components and time over which core stage pre-emulsions were added. 2-ME was added as a 10% solution in water; amounts listed are grams 2-ME.

| Example Number | Water | 30% SLS | MAA | MMA | EA | BA | CD559 | BEI | TMPTA | 2-ME | Seed Charge | Core add time (min) |
|---|---|---|---|---|---|---|---|---|---|---|---|---|
| 19 | 285.3 | 7.58 | 76.6 | 49.28 | 50.4 | — | 46.8 | — | — | 0.06992 | 27.4 | 80 |
| 20 | 293.1 | 7.58 | 84.39 | 49.28 | 50.4 | — | 15.6 | — | — | 0.06992 | 33.1 | 80 |
| 21 | 294.08 | 7.58 | 105.48 | 61.6 | 63 | — | 19.5 | — | — | 0.0874 | 27.6 | 100 |
| 22 | 298.95 | 7.58 | 110.36 | 61.6 | 63 | — | — | 24.6 | — | 0.0874 | 28.3 | 100 |
| 23 | 289.2 | 7.58 | 26.49 | 14.78 | 15.12 | — | — | — | 0.05 | 0.021 | 81.3 | 24 |
| 24 | 289.2 | 7.58 | 92.96 | 56.9 | 58.2 | — | 36.04 | — | — | 0.0808 | 29.3 | 92 |
| 25 | 289.2 | 7.58 | 92.96 | 56.9 | 58.2 | — | 36.04 | — | — | 0.0808 | 29.3 | 92 |
| 26 | 289.2 | 7.58 | 80.49 | 49.28 | 50.4 | — | 31.2 | — | — | 0.0699 | 31.5 | 80 |
| 27 | 289.2 | 7.58 | 80.49 | 49.28 | 50.4 | — | 31.2 | — | — | 0.0699 | 31.5 | 80 |
| 28 | 289.2 | 7.58 | 92.96 | 56.9 | 58.2 | — | 36.04 | — | — | — | 29.2 | 92 |
| 29 | 289.2 | 7.58 | 100.61 | 61.6 | 63 | — | 39 | — | — | — | 28.1 | 100 |

TABLE 1B

Shell stage of Examples 1-29. Gram amounts of components, time over which shell stage components were added, and mass percent of shell stage. 2-ME was added as a 10% solution in water; amounts listed are grams 2-ME.

| Example Number | MAA | MMA | EA | CD559 | BEI | TMPTA | EGDMA | DAP | 2-ME | Shell add time (min) | Mass % shell |
|---|---|---|---|---|---|---|---|---|---|---|---|
| 1 | 20.12 | 12.32 | 12.6 | 7.81 | — | 4.197 | — | — | 0.0175 | 20 | 16% |
| 2 | 20.12 | 12.32 | 12.6 | 7.81 | — | 2.0985 | — | — | 0.0175 | 10 | 16% |
| 3 | 20.12 | 12.32 | 12.6 | 7.81 | — | 2.0985 | — | — | 0.0175 | 20 | 16% |
| 4 | 20.12 | 12.32 | 12.6 | 7.81 | — | 3.3562 | — | — | 0.0175 | 20 | 16% |
| 5 | 20.12 | 12.32 | 12.6 | — | — | 4.197 | — | — | 0.0175 | 20 | 16% |
| 6 | 20.12 | 12.32 | 12.6 | 7.81 | — | 5.4561 | — | — | 0.0175 | 20 | 16% |
| 7 | 27.47 | 8.08 | 8.33 | 7.81 | — | 4.197 | — | — | 0.0175 | 20 | 16% |
| 8 | 14.6 | 15.53 | 15.80 | 7.81 | — | 4.197 | — | — | 0.0175 | 20 | 16% |
| 9 | 20.12 | 12.32 | 12.6 | 7.81 | — | — | 4.2116 | — | 0.0175 | 20 | 16% |
| 10 | 20.12 | 12.32 | 12.6 | 7.81 | — | — | — | 5.2324 | 0.0175 | 20 | 16% |
| 11 | 20.12 | 12.32 | 12.6 | 7.81 | — | 4.197 | — | — | 0.0175 | 20 | 16% |
| 12 | 22.07 | 12.32 | 12.6 | — | — | 4.197 | — | — | 0 | 20 | 16% |
| 13 | 20.12 | 12.32 | 12.6 | 7.81 | — | 4.197 | — | — | 0.0175 | 20 | 16% |
| 14 | 55.2 | 30.8 | 31.5 | — | — | 10.4925 | — | — | 0.04375 | 50 | 40% |
| 15 | 50.3 | 30.8 | 31.5 | 19.52 | — | 10.4925 | — | — | 0.04375 | 50 | 40% |
| 16 | 22.07 | 12.32 | 12.6 | — | — | 4.197 | — | — | 0.0175 | 20 | 16% |
| 17 | 20.12 | 12.32 | 12.6 | 7.81 | — | 4.197 | — | — | 0.0175 | 20 | 16% |
| 18 | 19.14 | 12.32 | 12.6 | 11.71 | — | 4.197 | — | — | 0.0175 | 20 | 16% |
| 19 | 43.04 | 25.13 | 25.7 | 23.9 | — | 8.5619 | — | — | 0.0357 | 40 | 34% |
| 20 | 43.04 | 25.13 | 25.7 | 7.96 | — | 8.5619 | — | — | 0.0357 | 40 | 34% |
| 21 | 21.1 | 12.32 | 12.6 | 3.905 | — | 4.197 | — | — | 0.0175 | 20 | 16% |
| 22 | 22.07 | 12.32 | 12.6 | — | 4.93 | 4.197 | — | — | 0.0175 | 20 | 16% |
| 23 | 96.58 | 59.14 | 60.48 | 37.6 | — | 2.4591 | — | — | 0.084 | 96 | 80% |
| 24 | 27.22 | 16.67 | 17.05 | 10.57 | — | 5.6783 | — | — | 0.0237 | 28 | 23% |
| 25 | 27.22 | 16.67 | 17.05 | 10.57 | — | 7.0979 | — | — | 0.0237 | 28 | 23% |
| 26 | 41.04 | 25.13 | 25.7 | 15.93 | — | 8.5619 | — | — | 0.0357 | 40 | 34% |
| 27 | 41.04 | 25.13 | 25.7 | 15.93 | — | 6.4214 | — | — | 0.0357 | 40 | 34% |
| 28 | 27.22 | 16.67 | 17.05 | 10.57 | — | 5.6783 | — | — | 0 | 14 | 23% |
| 29 | 20.12 | 12.32 | 12.6 | 7.81 | — | 4.197 | — | — | 0 | 20 | 16% |

TABLE 1C

Mole percentages of core stage components of Examples 1-29. Mole percentages of crosslinkers and 2-ME refers to the mole percent of crosslinker or 2-ME based on the total mole amounts of monomers not including the crosslinker and 2-ME.

| Example Number | MAA | MMA | EA | BA | CD-559 | BEI | TMPTA | 2-ME |
|---|---|---|---|---|---|---|---|---|
| 1 | 50.4 | 24.2 | 24.8 | — | 0.63 | — | — | 0.044 |
| 2 | 50.4 | 24.2 | 24.8 | — | 0.63 | — | — | 0.044 |
| 3 | 50.4 | 24.2 | 24.8 | — | 0.63 | — | — | 0.044 |
| 4 | 50.4 | 24.2 | 24.8 | — | 0.63 | — | — | 0.044 |
| 5 | 50.4 | 24.2 | 24.8 | — | 0.63 | — | — | 0.044 |
| 6 | 50.4 | 24.2 | 24.8 | — | 0.63 | — | — | 0.044 |
| 7 | 50.4 | 24.2 | 24.8 | — | 0.63 | — | — | 0.044 |
| 8 | 50.4 | 24.2 | 24.8 | — | 0.63 | — | — | 0.044 |
| 9 | 50.4 | 24.2 | 24.8 | — | 0.63 | — | — | 0.044 |
| 10 | 50.4 | 24.2 | 24.8 | — | 0.63 | — | — | 0.044 |
| 11 | 50.4 | 24.2 | 24.8 | — | 0.63 | — | 0.56 | 0.044 |
| 12 | 50.7 | 24.4 | 24.9 | — | 0.00 | — | — | — |

TABLE 1C-continued

Mole percentages of core stage components of Examples 1-29. Mole percentages of crosslinkers and 2-ME refers to the mole percent of crosslinker or 2-ME based on the total mole amounts of monomers not including the crosslinker and 2-ME.

| Example Number | MAA | MMA | EA | BA | CD-559 | BEI | TMPTA | 2-ME |
|---|---|---|---|---|---|---|---|---|
| 13 | 51.3 | 24.6 | 16.8 | 6.6 | 0.64 | — | — | 0.044 |
| 14 | 50.4 | 24.2 | 24.8 | — | 0.63 | — | — | 0.044 |
| 15 | 50.4 | 24.2 | 24.8 | — | 0.63 | — | — | 0.044 |
| 16 | 50.7 | 24.4 | 24.9 | — | 0.00 | — | — | 0.044 |
| 17 | 50.7 | 24.4 | 24.9 | — | 0.00 | — | — | 0.044 |
| 18 | 50.3 | 24.1 | 24.7 | — | 0.94 | — | — | 0.044 |
| 19 | 50.3 | 24.1 | 24.7 | — | 0.94 | — | — | 0.044 |
| 20 | 50.6 | 24.3 | 24.8 | — | 0.32 | — | — | 0.044 |
| 21 | 50.6 | 24.3 | 24.8 | — | 0.32 | — | — | 0.044 |
| 22 | 50.4 | 24.2 | 24.8 | — | 0.00 | 0.6 | — | 0.044 |
| 23 | 50.7 | 24.4 | 24.9 | — | 0.00 | — | 0.05 | 0.044 |
| 24 | 50.4 | 24.2 | 24.8 | — | 0.63 | — | — | 0.044 |
| 25 | 50.4 | 24.2 | 24.8 | — | 0.63 | — | — | 0.044 |
| 26 | 50.4 | 24.2 | 24.8 | — | 0.63 | — | — | 0.044 |
| 27 | 50.4 | 24.2 | 24.8 | — | 0.63 | — | — | 0.044 |
| 28 | 50.4 | 24.2 | 24.8 | — | 0.63 | — | — | — |
| 29 | 50.4 | 24.2 | 24.8 | — | 0.63 | — | — | — |

TABLE 1D

Mole percentages of shell stage components of Examples 1-29. Mole percentages of crosslinkers and 2-ME refers to the mole percent of crosslinker or 2-ME based on the total mole amounts of monomers not including the crosslinkers and 2-ME.

| Example Number | MAA | MMA | EA | CD-559 | BEI | TMPTA | EGDMA | DAP | 2-ME |
|---|---|---|---|---|---|---|---|---|---|
| 1 | 50.4 | 24.2 | 24.8 | 0.63 | — | 2.79 | — | — | 0.044 |
| 2 | 50.4 | 24.2 | 24.8 | 0.63 | — | 1.40 | — | — | 0.044 |
| 3 | 50.4 | 24.2 | 24.8 | 0.63 | — | 1.40 | — | — | 0.044 |
| 4 | 50.4 | 24.2 | 24.8 | 0.63 | — | 1.40 | — | — | 0.044 |
| 5 | 48.4 | 25.5 | 26.1 | 0.00 | — | 2.79 | — | — | 0.046 |
| 6 | 50.4 | 24.2 | 24.8 | 0.63 | — | 2.79 | — | — | 0.044 |
| 7 | 67.2 | 15.9 | 16.4 | 0.63 | — | 2.79 | — | — | 0.044 |
| 8 | 37.8 | 30.5 | 31.0 | 0.63 | — | 2.79 | — | — | 0.044 |
| 9 | 50.4 | 24.2 | 24.8 | 0.63 | — | — | 4.18 | — | 0.044 |
| 10 | 50.4 | 24.2 | 24.8 | 0.63 | — | — | — | 4.18 | 0.044 |
| 11 | 50.4 | 24.2 | 24.8 | 0.63 | — | 2.79 | — | — | 0.044 |
| 12 | 50.7 | 24.4 | 24.9 | 0.00 | — | 2.80 | — | — | — |
| 13 | 50.4 | 24.2 | 24.8 | 0.63 | — | 2.79 | — | — | 0.044 |
| 14 | 50.7 | 24.4 | 24.9 | 0.00 | — | 2.79 | — | — | 0.044 |
| 15 | 50.4 | 24.2 | 24.8 | 0.63 | — | 2.79 | — | — | 0.044 |
| 16 | 50.7 | 24.4 | 24.9 | 0.00 | — | 2.80 | — | — | 0.044 |
| 17 | 50.4 | 24.2 | 24.8 | 0.63 | — | 2.79 | — | — | 0.044 |
| 18 | 50.2 | 24.1 | 24.7 | 0.94 | — | 2.79 | — | — | 0.043 |
| 19 | 52.4 | 23.1 | 23.6 | 0.90 | — | 2.79 | — | — | 0.042 |
| 20 | 50.6 | 24.3 | 24.8 | 0.32 | — | 2.79 | — | — | 0.044 |
| 21 | 50.6 | 24.3 | 24.8 | 0.32 | — | 2.79 | — | — | 0.044 |
| 22 | 50.4 | 24.2 | 24.8 | 0.00 | 0.6 | 2.79 | — | — | 0.044 |
| 23 | 50.4 | 24.2 | 24.7 | 0.63 | — | 0.34 | — | — | 0.044 |
| 24 | 50.4 | 24.2 | 24.8 | 0.63 | — | 2.79 | — | — | 0.044 |
| 25 | 50.4 | 24.2 | 24.8 | 0.63 | — | 3.49 | — | — | 0.044 |
| 26 | 50.4 | 24.2 | 24.8 | 0.63 | — | 2.09 | — | — | 0.044 |
| 27 | 50.4 | 24.2 | 24.8 | 0.63 | — | 2.79 | — | — | 0.044 |
| 28 | 50.4 | 24.2 | 24.8 | 0.63 | — | 2.79 | — | — | — |
| 29 | 50.4 | 24.2 | 24.8 | 0.63 | — | 2.79 | — | — | — |

TABLE 2A

Core stages of Examples 30-33. Gram amounts of components and time over which core stage monomer mixtures were added. 2-ME was added as a 10% solution in water; amounts listed are grams 2-ME.

| Example Number | Monomer mixture components | | | | | | Core add time (min) |
|---|---|---|---|---|---|---|---|
| | MAA | MMA | EA | CD559 | TMPTA | 2-ME | |
| 30 | 12.07 | 7.39 | 7.56 | 4.68 | — | 0.0105 | 7 |
| 31 | 42.26 | 25.87 | 26.46 | 16.38 | — | 0.0367 | 39 |
| 32 | 12.07 | 7.39 | 7.56 | 4.68 | — | 0.0105 | 7 |
| 33 | 42.26 | 25.87 | 26.46 | 16.38 | — | 0.0367 | 39 |

TABLE 2B

Shell stages of Examples 30-33. Gram amounts of components, time over which shell stage components were added, and mass percent of shell stage. 2-ME was added as a 10% solution in water; amounts listed are grams 2-ME.

| Example Number | MAA | MMA | EA | CD559 | TMPTA | 2-ME | Shell add time (min) | Mass % shell |
|---|---|---|---|---|---|---|---|---|
| 30 | 108.65 | 66.53 | 68.04 | 42.174 | 11.3319 | 0.0945 | 104 | 90% |
| 31 | 78.47 | 48.05 | 49.14 | 30.46 | 16.3683 | 0.0683 | 78 | 65% |
| 32 | 108.65 | 66.53 | 68.04 | 42.174 | 6.7991 | 0.0945 | 104 | 90% |
| 33 | 78.47 | 48.05 | 49.14 | 30.46 | 13.0946 | 0.0683 | 78 | 65% |

TABLE 2C

Mole percentages of core stage components of Examples 30-33.

| Example Number | MAA | MMA | EA | CD559 | 2-ME |
|---|---|---|---|---|---|
| 30 | 50.4 | 24.2 | 24.8 | 0.63 | 0.044 |
| 31 | 50.4 | 24.2 | 24.8 | 0.63 | 0.044 |
| 32 | 50.4 | 24.2 | 24.8 | 0.63 | 0.044 |
| 33 | 50.4 | 24.2 | 24.8 | 0.63 | 0.044 |

TABLE 2D

Mole percentages of shell stage components of Examples 30-33. Mole percentages of crosslinker and 2-ME refer to the mole percent of crosslinker or 2-ME based on the total mole amounts of monomers not including the crosslinker and 2-ME.

| Example Number | MAA | MMA | EA | CD559 | TMPTA | 2-ME |
|---|---|---|---|---|---|---|
| 30 | 50.4 | 24.2 | 24.8 | 0.63 | 1.39 | 0.044 |
| 31 | 50.4 | 24.2 | 24.8 | 0.63 | 2.79 | 0.044 |
| 32 | 50.4 | 24.2 | 24.8 | 0.63 | 0.84 | 0.044 |
| 33 | 50.4 | 24.2 | 24.8 | 0.63 | 2.23 | 0.044 |

Example 34 Ethoxylated TMPTA Example in Shell with Associative Monomer

Into a 1 L reactor is added 247 g water and 7.58 g of 30% sodium laurel sulfate solution. The contents are heated to 85 C with overhead stirring and constant overhead nitrogen flow. A monomer pre-emulsion is prepared in a solution of 289.2 g water and 7.58 g of 30% sodium laurel sulfate contained in a graduated cylinder with overhead stirring. To this solution is added 39 g of 50% CD-559 associative monomer (0.016 moles) in 25/25 wt % water/methacrylic acid (0.11 moles), 0.0874 g 2-mercaptoethanol (0.011 moles) as a 10% solution in water, 100.61 g of methacrylic acid (1.17 moles), 61.6 g of methyl methacrylate (0.62 moles), and 63 g of ethyl acrylate (0.63 moles). When the reactor contents at the set temperature for 1 hr, a seed stage is commenced by feeding into the reactor 5 wt % of the monomer pre-emulsion subsurface, into the reactor contents. The reactor contents are stirred for 15 minutes, at which time a solution of 0.31 g ammonium persulfate in 17.5 g of water is shot into the reactor, and the stirring continues for another 15 minutes.

Core stage: The core stage feed commences as the monomer pre-emulsion is fed into the reactor contents subsurface over a period of 100 minutes, concurrent with a separate initiator solution of 0.29 g ammonium persulfate in 62.8 g of water fed at a rate of 0.32 g/min.

Shell stage: When the monomer pre-emulsion cylinder contents are empty, a monomer mixture comprising 7.81 g of 50% CD-559 associative monomer (0.003 moles) in 25/25 wt % water/methacrylic acid (0.023 moles), 0.0175 g 2-mercaptoethanol (0002 moles) as a 10% solution in water, 4.197 g (0.066 moles) trimethyolpropane(ethoxylate) triacrylate (Komerate T-093 available from KPX Green Chemical), 20.12 g of methacrylic acid (0.23 moles), 12.32 g of methyl methacrylate (0.12 moles), and 12.6 g of ethyl acrylate (0.12 moles) is added subsurface to the reactor contents over a period of 20 minutes. The initiator solution described above continues to be fed simultaneously with no change in rate.

When the monomer mixture feed has finished, the initiator solution feed rate is doubled and is fed to completion, at which point the reactor temperature is increased to 90 C and the contents are cooked for one hour. The reactor contents are cooled to ambient and the product is a white emulsion.

Example 35

Into a 1 L reactor was added 495.8 g water and 1.17 g of 30% sodium laurel sulfate solution. The contents were heated to 84° C. with overhead stirring and constant overhead nitrogen flow. A monomer pre-emulsion was prepared in a solution of 25.38 g water and 2.47 g of 30% sodium laurel sulfate contained in a graduated cylinder with overhead stirring. To this solution was added 14.41 g of methacrylic acid (0.167 moles), 11.55 g 96% 2-hydroxyethyl acrylate (0.095 moles), 48.25 g of ethyl acrylate (0.482 moles), and 0.111 g TMPTA (0.00038 moles). When the reactor contents had reached 84° C., an initiator solution of 0.1998 g ammonium persulfate in 9.79 g of water was shot into the reactor.

Core stage: The core stage feed commenced as the monomer pre-emulsion was fed into the reactor contents subsurface over a period of 30 minutes.

Shell stage: When the monomer pre-emulsion cylinder contents were empty, a monomer pre-emulsion comprising 101.53 g water, 9.87 g 30% sodium laurel sulfate, 192.77 g ethyl acrylate (1.93 moles), 46.25 g 96% 2-hydroxyethyl acrylate (0.38 moles), 57.72 g methacrylic acid (0.67 moles), and 1.11 g TMPTA (0.0037 moles) in a graduated cylinder with overhead stirring was added subsurface to the reactor contents over a period of 120 minutes. Upon completion of the monomer pre-emulsion and initiator slow-adds, the reactor contents continued to be stirred at temperature for 150 minutes. The reactor contents were cooled to ambient and the product was a white emulsion.

Example 36 (Multistage 1)

Into a 1 L reactor is added 247 g water and 7.58 g of 30% sodium laurel sulfate solution. The contents are heated to 85

C with overhead stirring and constant overhead nitrogen flow. A monomer pre-emulsion is prepared in a solution of 289.2 g water and 7.58 g of 30% sodium laurel sulfate contained in a graduated cylinder with overhead stirring. To this solution is added 39 g of 50% CD-559 associative monomer (0.016 moles) in 25/25 wt % water/methacrylic acid (0.11 moles), 0.0874 g 2-mercaptoethanol (0.0011 moles) as a 10% solution in water, 0.2 g TMPTA (0.0007 moles), 100.61 g of methacrylic acid (1.17 moles), 61.6 g of methyl methacrylate (0.62 moles), and 63 g of ethyl acrylate (0.63 moles). When the reactor contents have been at the set temperature for 1 hr, a seed stage is commenced by feeding into the reactor 5 wt % of the monomer pre-emulsion subsurface, into the reactor contents. The reactor contents are stirred for 15 minutes, at which time a solution of 0.31 g ammonium persulfate in 17.5 g of water is shot into the reactor, and the stirring continues for another 15 minutes.

Core stage: The core stage feed commences as the monomer pre-emulsion is fed into the reactor contents subsurface over a period of 100 minutes, concurrent with a separate initiator solution of 0.29 g ammonium persulfate in 62.8 g of water fed at a rate of 0.32 g/min.

First shell stage: When the monomer pre-emulsion cylinder contents are empty, a monomer mixture comprising 3.9 g of 50% CD-559 associative monomer (0.0016 moles) in 25/25 wt % water/methacrylic acid (0.011 moles), 0.0087 g 2-mercaptoethanol (0.00011 moles) as a 10% solution in water, 3.1478 g TMPTA (0.011 moles), 10.06 g of methacrylic acid (0.117 moles), 6.16 g of methyl methacrylate (0.062 moles), and 6.3 g of ethyl acrylate (0.063 moles is added subsurface to the reactor contents over a period of 10 minutes. The initiator solution described above continues to be fed simultaneously with no change in rate.

Second shell stage: When monomer feed of the first shell stage is completed, a monomer mixture comprising 3.9 g of 50% CD-559 associative monomer (0.0016 moles) in 25/25 wt % water/methacrylic acid (0.011 moles), 0.0087 g 2-mercaptoethanol (0.00011 moles) as a 10% solution in water, 1.0492 g TMPTA (0.0035 moles), 10.06 g of methacrylic acid (0.117 moles), 6.16 g of methyl methacrylate (0.062 moles), and 6.3 g of ethyl acrylate (0.063 moles) is added subsurface to the reactor contents over a period of 10 minutes. The initiator solution described above continues to be fed simultaneously with no change in rate.

When the second shell stage monomer feed is finished, the initiator solution feed rate is doubled and is fed to completion, at which point the reactor temperature is increased to 90 C and the contents are cooked for one hour. The reactor contents are cooled to room temperature and 47 g of water are added to the emulsion thus produced.

Example 37 (Multistage 2)

Into a 1 L reactor is added 247 g water and 7.58 g of 30% sodium laurel sulfate solution. The contents are heated to 85 C with overhead stirring and constant overhead nitrogen flow. A monomer pre-emulsion is prepared in a solution of 289.2 g water and 7.58 g of 30% sodium laurel sulfate contained in a graduated cylinder with overhead stirring. To this solution is added 39 g of 50% CD-559 associative monomer (0.016 moles) in 25/25 wt % water/methacrylic acid (0.11 moles), 0.0874 g 2-mercaptoethanol (0.0011 moles) as a 10% solution in water, 0.2 g TMPTA (0.0007 moles), 100.61 g of methacrylic acid (1.17 moles), 61.6 g of methyl methacrylate (0.62 moles), and 63 g of ethyl acrylate (0.63 moles). When the reactor contents have been at the set temperature for 1 hr, a seed stage is commenced by feeding into the reactor 5 wt % of the monomer pre-emulsion subsurface, into the reactor contents. The reactor contents are stirred for 15 minutes, at which time a solution of 0.31 g ammonium persulfate in 17.5 g of water is shot into the reactor, and the stirring continues for another 15 minutes.

Core stage: The core stage feed commences as the monomer pre-emulsion is fed into the reactor contents subsurface over a period of 100 minutes, concurrent with a separate initiator solution of 0.29 g ammonium persulfate in 62.8 g of water fed at a rate of 0.32 g/min.

First shell stage: When the monomer pre-emulsion cylinder contents are empty, a monomer mixture comprising 3.9 g of 50% CD-559 associative monomer (0.0016 moles) in 25/25 wt % water/methacrylic acid (0.11 moles), 0.0087 g 2-mercaptoethanol (0.00011 moles) as a 10% solution in water, 1.0492 g TMPTA (0.0035 moles), 10.06 g of methacrylic acid (0.117 moles), 6.16 g of methyl methacrylate (0.062 moles), and 6.3 g of ethyl acrylate (0.063 moles) is added subsurface to the reactor contents over a period of 10 minutes. The initiator solution described above continues to be fed simultaneously with no change in rate.

Second shell stage: When monomer feed of the first shell stage is completed, a monomer mixture comprising 3.9 g of 50% CD-559 associative monomer (0.0016 moles) in 25/25 wt % water/methacrylic acid (0.011 moles), 0.0087 g 2-mercaptoethanol (0.00011 moles) as a 10% solution in water, 3.1478 g TMPTA (0.0106 moles), 10.06 g of methacrylic acid (0.117 moles), 6.16 g of methyl methacrylate (0.062 moles), and 6.3 g of ethyl acrylate (0.063 moles) is added subsurface to the reactor contents over a period of 10 minutes. The initiator solution described above continues to be fed simultaneously with no change in rate.

When monomer feed of the second shell stage is finished, the initiator solution feed rate is doubled and is fed to completion, at which point the reactor temperature is increased to 90 C and the contents are cooked for one hour. The reactor contents are cooled to room temperature and 47 g of water are added to the emulsion thus produced.

Example 38 Less Ionic-Shell Example

Into a 1 L reactor is added 495.8 g water and 1.17 g of 30% sodium laurel sulfate solution. The contents are heated to 84 C with overhead stirring and constant overhead nitrogen flow. A monomer pre-emulsion is prepared in a solution of 25.38 g water and 2.47 g of 30% sodium laurel sulfate contained in a graduated cylinder with overhead stirring. To this solution is added 14.41 g of methacrylic acid (0.167 moles), 11.55 g 96% 2-hydroxyethyl acrylate (0.095 moles), 48.25 g of ethyl acrylate (0.482 moles), and 0.111 g TMPTA (0.00038 moles). When the reactor contents reach 84° C., an initiator solution of 0.1998 g ammonium persulfate in 9.79 g of water is shot into the reactor.

Core stage: The core stage feed commences as the monomer pre-emulsion is fed into the reactor contents subsurface over a period of 30 minutes.

Shell stage: When the monomer pre-emulsion cylinder contents are empty, a monomer pre-emulsion comprising 101.53 g water, 9.87 g 30% sodium laurel sulfate, 192.77 g ethyl acrylate (1.93 moles), 30 g 96% 2-hydroxyethyl acrylate (0.248 moles), 57.72 g methacrylic acid (0.67 moles), and 1.11 g TMPTA (0.0037 moles) in a graduated cylinder with overhead stirring is added subsurface to the reactor contents over a period of 120 minutes. Upon completion of the monomer pre-emulsion and initiator slow-adds, the reactor contents continue to be stirred at temperature for 150 minutes. The reactor contents are cooled to ambient and the product is a white emulsion.

Example 39 More Ionic-Shell Example

Into a 1 L reactor is added 495.8 g water and 1.17 g of 30% sodium laurel sulfate solution. The contents are heated to 84 C with overhead stirring and constant overhead nitrogen flow. A monomer pre-emulsion is prepared in a solution of 25.38 g water and 2.47 g of 30% sodium laurel sulfate contained in a graduated cylinder with overhead stirring. To this solution is added 14.41 g of methacrylic acid (0.167 moles), 11.55 g 96% 2-hydroxyethyl acrylate (0.095 moles), 48.25 g of ethyl acrylate (0.482 moles), and 0.111 g TMPTA (0.00038 moles). When the reactor contents reach 84° C., an initiator solution of 0.1998 g ammonium persulfate in 9.79 g of water is shot into the reactor.

Core stage: The core stage feed commences as the monomer pre-emulsion is fed into the reactor contents subsurface over a period of 30 minutes.

Shell stage: When the monomer pre-emulsion cylinder contents are empty, a monomer pre-emulsion comprising 101.53 g water, 9.87 g 30% sodium laurel sulfate, 192.77 g ethyl acrylate (1.93 moles), 55 g 96% 2-hydroxyethyl acrylate (0.454 moles), 57.72 g methacrylic acid (0.67 moles), and 1.11 g TMPTA (0.0037 moles) in a graduated cylinder with overhead stirring is added subsurface to the reactor contents over a period of 120 minutes. Upon completion of the monomer pre-emulsion and initiator slow-adds, the reactor contents continue to be stirred at temperature for 150 minutes. The reactor contents are cooled to ambient and the product is a white emulsion.

Examples 40-69 Hair Gel Formulations with Wet Materials Neutralized to 80%

Core/shell emulsion polymers of Examples 1-29 and 35 were each formulated into separate hair gel compositions with the components and amounts listed in Table 3.

Hair gels were formulated in accordance with the following procedure:

Water was dispensed into a beaker. To this was added the emulsion in an amount to provide 2.63 wt % of the active core-shell polymer in the total formulation. The mixture was agitated with overhead mixing at a speed of 500-800 RPM. A quantity of 95% AMP Ultra PC 2000 (available from Angus Chemical, IL) was added to the mixture in an amount appropriate to neutralize 80% of the acid groups within the core/shell polymer emulsion to obtain a pH of ~6.6-7.3. The mixture was agitated for 30 minutes, at which time the preservative (Glydant Plus available from Lonza Personal Care, NJ) was added in the amount of 0.5 wt % of the total formulation. The samples were centrifuged for 1 to 15 minutes to remove excess air.

After 24 hours, viscosities of the gel samples were measured with a Brookfield RVDVI-Prime affixed with Helipath attachment model D using Spindle D/10 at 10 RPM, and sample turbidities were measured, with results listed in Table 3. Turbidity is determined by the use of a 2100 N Turbidimeter available from the Hach Company, CO via the following procedure: After the instrument has been powered on it is allowed to warm up for several minutes until it registers a number on the display, indicating it is ready to read samples. The gel sample is dispensed into a 30 mL vial and the vial exterior is wiped clean with a cloth that has been dampened with silicone oil. The vial is placed in the instrument sample compartment, and the index mark on the vial is aligned with the black indicator mark in the sample compartment. The sample compartment cover is closed and the instrument automatically reads and reports the turbidity of the sample in NTU on the display.

TABLE 3

Hair gel Examples 40-69. No preservative was added to Example 69.

| Example Number | Water | Polymer | pH | Turbdity (NTU) | Viscosity (kcps) |
|---|---|---|---|---|---|
| 40 | q.s. to 100% | Example 1 | 7 | 34.2 | 110 |
| 41 | q.s. to 100% | Example 2 | 6.77 | 28.8 | 88.2 |
| 42 | q.s. to 100% | Example 3 | 6.8 | 10.2 | 103 |
| 43 | q.s. to 100% | Example 4 | 6.57 | 29 | 88.6 |
| 44 | q.s. to 100% | Example 5 | 7 | 61 | 104 |
| 45 | q.s. to 100% | Example 6 | 6.5 | 61 | 93 |
| 46 | q.s. to 100% | Example 7 | 7.3 | 52 | 109 |
| 47 | q.s. to 100% | Example 8 | 7.1 | 106 | 171 |
| 48 | q.s. to 100% | Example 9 | 6.79 | 15.5 | 131 |
| 49 | q.s. to 100% | Example 10 | 6.92 | 5.49 | 133 |
| 50 | q.s. to 100% | Example 11 | 7.13 | 506 | 36.4 |
| 51 | q.s. to 100% | Example 12 | 6.72 | 24.2 | 2 |
| 52 | q.s. to 100% | Example 13 | 7.07 | 29.6 | 112 |
| 53 | q.s. to 100% | Example 14 | 6.81 | 130 | 70.4 |
| 54 | q.s. to 100% | Example 15 | 7.07 | 199 | 62.8 |
| 55 | q.s. to 100% | Example 16 | 6.95 | 28.5 | 1.2 |
| 56 | q.s. to 100% | Example 17 | 7.26 | 15.9 | 1.8 |
| 57 | q.s. to 100% | Example 18 | 7.33 | 80.4 | 178 |
| 58 | q.s. to 100% | Example 19 | 7.33 | 80.4 | 128 |
| 59 | q.s. to 100% | Example 20 | 6.89 | 175 | 40.2 |
| 60 | q.s. to 100% | Example 21 | 7.23 | 22.2 | 73.2 |
| 61 | q.s. to 100% | Example 22 | 6.57 | 25.6 | 180 |
| 62 | q.s. to 100% | Example 23 | 6.61 | 53.9 | 38.4 |
| 63 | q.s. to 100% | Example 24 | 7.04 | 57 | 112.3 |
| 64 | q.s. to 100% | Example 25 | 7.04 | 56.5 | 94.2 |
| 65 | q.s. to 100% | Example 26 | 6.48 | 85.9 | 38.8 |
| 66 | q.s. to 100% | Example 27 | 6.87 | 82.2 | 76.2 |
| 67 | q.s. to 100% | Example 28 | 6.74 | 87.9 | 47 |
| 68 | q.s. to 100% | Example 29 | 6.72 | 28.6 | 107 |
| 69 | q.s. to 100% | Example 35 | 7 | 253 | 37.8 |

Example 70 Carbopol 980/Example 1 Mixture Gel 90.9 g of water was dispensed into a beaker. To this was added 6.7 g of Example 1. The mixture was agitated with overhead mixing at a speed of 500-800 RPM and 0.2 g of Carbopol 980 (available from Lubrizol) was dispensed into the mixture. The mixture was agitated for 30 minutes. 1.7 g of triethanolamine was dispensed into the mixture and the forming gel is agitated an additional 30 minutes, at which time 0.5 g preservative (Glydant Plus available from Lonza) is added. The result was a thick hair gel.

Examples 71-78 Hair Gel Formulations with Wet Materials Neutralized to 90%

Core/shell emulsion polymers of the invention were each formulated into separate hair gel compositions with the components listed in Table 4.

The hair gels were formulated in accordance with the following procedure:

Water was dispensed into a beaker. To this was added the emulsion polymer of the invention. The mixture was agitated with overhead mixing at a speed of 500-800 RPM. A quantity of AMP Ultra PC 2000 was added to the mixture in an amount appropriate to neutralize 90% of the acid groups within the core/shell polymer emulsion to obtain a pH of ~6.6-7.3. The mixture was agitated for 30 minutes, at which time the preservative (Glydant Plus) was added. The samples were centrifuged for 1 to 15 minutes to remove excess air.

TABLE 4

| Example | Water | 95% AMP Ultra 2000 to neutralization | Polymer | Polymer wt % active | Glydant Plus wt % |
| --- | --- | --- | --- | --- | --- |
| 71 | q.s. to 100% | 90% | Example 4 | 2.63 | 0.5 |
| 72 | q.s. to 100% | 90% | Example 6 | 2.63 | 0.5 |
| 73 | q.s. to 100% | 90% | Example 9 | 2.63 | 0.5 |
| 74 | q.s. to 100% | 90% | Example 10 | 2.63 | 0.5 |
| 75 | q.s. to 100% | 90% | Example 1 | 2.63 | 0.5 |
| 76 | q.s. to 100% | 90% | Example 24 | 2.63 | 0.5 |
| 77 | q.s. to 100% | 90% | Example 27 | 2.63 | 0.5 |
| 78 | q.s. to 100% | 90% | Example 15 | 2.63 | 0.5 |

Example 79 Spray Dry Procedure, Dry Material Example

A core/shell emulsion polymer having the composition of Example 1 was diluted with water to 20% solid content. To the dilute emulsion was added a 20% solution of DE 5 maltodextrin to create a 20% solution whose solid content was 75 weight percent core/shell polymer, and 25 weight percent maltodextrin.

The 20% polymer/maltodextrin solution was spray dried using a Mobile Minor Spray Dryer from GEA, Niro. Prior to spray drying, the Mobile Minor was heated to and held at 100° C. until stable conditions were established. Polished water was fed through the inlet tube until no condensation in either the dryer or receiver was visible, and then the feed line was switched over to the 20% polymer/maltodextrin solution. The emulsion concentration in the feed line progressively increased to 100% as the startup polished water feed was consumed and pushed out of the feed line to the nozzle and then through the dryer. The dry polymer/maltodextrin powder at the end of the process was collected.

Examples 80, 81 Hair Gel Formulations with Dry Materials Neutralized to 80%

Polymer/maltodextrin powders of the composition of Example 79 were formulated into hair gel compositions with the components listed in Table 5 and according to the procedure below.

TABLE 5

| Example | Water wt % | 95% AMP Ultra 2000 to neutralization | Polymer | Polymer wt % active | Glydant Plus wt % |
| --- | --- | --- | --- | --- | --- |
| 80 | q.s. to 100% | 80% | Example 79 | 2.63 | 0.5 |
| 81 | q.s. to 100% | 90% | Example 79 | 2.63 | 0.5 |

Dry maltodextrin/polymer powder was dispersed into water with overhead stirring at 200-300 RPM for 30 minutes. Stirring speed was increased to 500-800 RPM, neutralizer was added (AMP Ultra PC 2000) to the contents in an amount appropriate to neutralize 80% or 90% of the acid groups within the core/shell polymer, and stirring continued for 30 minutes. A preservative (Glydant Plus) was then added and mixed into the gel sample. Samples were centrifuged to remove excess air.

Example 82—High Humidity Curl Retention

It may be desirable for a hair gel to maintain the hold and shape of styled hair for several hours. In humid conditions, the gel may lose its ability to maintain hold and shape over time. The following procedure was used to evaluate the ability of the polymers of the invention, formulated into hair gels as described above, to maintain the hold and shape of styled hair over several hours and in humid conditions.

Figure 2:
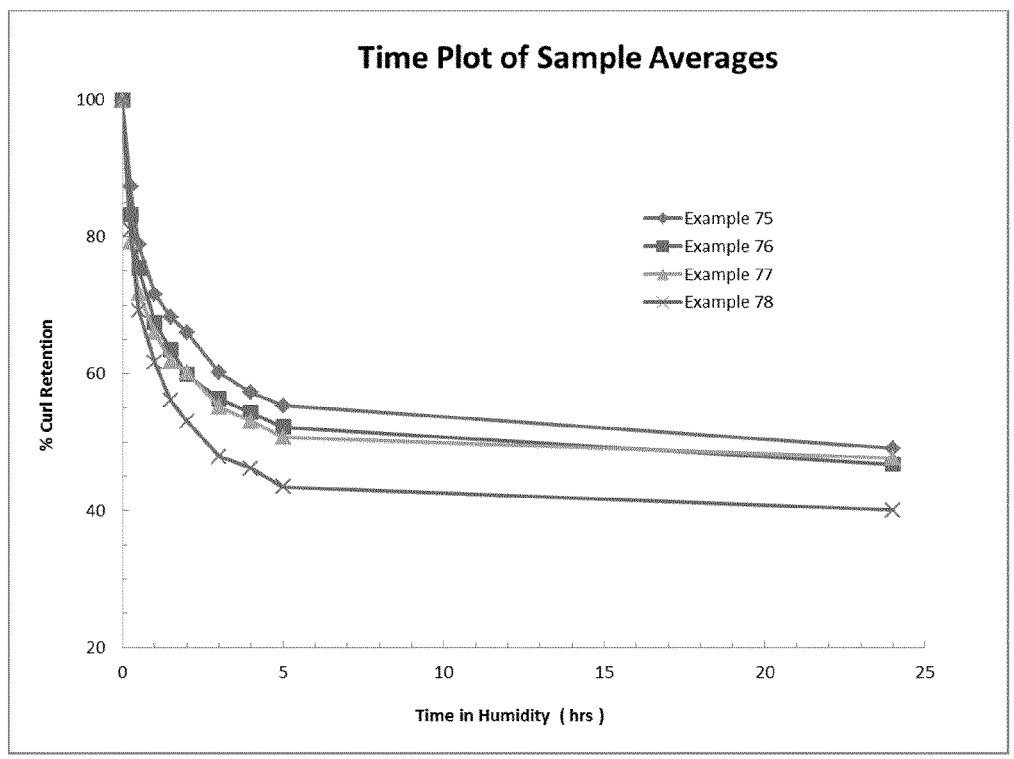
FIG. 2 is a graph of percent curl retention over time in a high humidity curl retention evaluation of hair gel formulations of Examples 75-78, evaluated as described in Example 82.

Half a gram of each of the hair gel formulations of Examples 71-78 were applied to 10 inch long, 2 gram swatches of damp hair, and worked until the hair was evenly coated. The hair ("tress" or "swatch") was then curled around a 0.5 inch Teflon mandrel. The curled tress was removed and clipped together on each end. Nine replicates were prepared in this manner for each sample. The curls were then placed in a 120° F. oven overnight to dry. The curled tresses were removed from the oven the next day and allowed to cool to room temperature for approximately 15-20 minutes before being suspended from the bound end of the swatch on graduated, clear, transparent curl retention boards. The clips were then removed and the tresses were unwound using a glass rod. An initial length was recorded before the boards were placed in a humidity chamber, which provided conditions of 70° F. and 90% relative humidity. Length readings were then recorded at 15 minute, 30 minute, 60 minute, 90 minute, 2 hour, 3 hour, 4 hour, 5 hour, and 24 hour intervals. The swatches and boards were then removed from the humidity chamber and the percent retention of the curls ("high humidity curl retention") was obtained. The results are shown in FIGS. 1 and 2.

Example 83 No Associative, No Crosslinker in Core, >3 Mol % Crosslinker in Shell, >40% Shell A solution of 247 g water and 7.58 g sodium lauryl sulfate 30% solution is prepared as the initial charge in a 1 L reactor. The reactor contents are heated to 85° C. with overhead stirring and an overhead nitrogen sparge. A surfactant solution comprising 289.2 g water and 7.58 g sodium laurel sulfate 30% solution is prepared in a graduated cylinder. In a separate graduated cylinder a monomer mixture comprising 46.35 g methacrylic acid (0.54 moles), 25.87 g methyl methacrylate (0.26 moles), 26.46 g ethyl acrylate (0.26 moles), and 0.367 g 2-mercaptoethanol (0.005 moles) as a 10% solution in water is prepared. When the reactor contents have been at temperature for one hour, 12 weight percent of the monomer mixture and then 5 weight percent of the surfactant solution in the graduated cylinder are quickly shot into the reactor. The reactor contents are stirred for 15 minutes, at which time an initiator solution containing 0.31 g sodium persulfate dissolved in 17.5 g water is added to the reactor contents. The reactor contents are agitated for another 15 minutes.

Core stage: The core stage feed commences as the monomer pre-emulsion is fed into the reactor contents subsurface over a period of 39 minutes, concurrent with a separate initiator solution of 0.29 g ammonium persulfate in 62.8 g of water fed at a rate of 0.32 g/min.

Shell stage: When the monomer pre-emulsion cylinder contents are empty, a monomer mixture comprising 0.0683 g 2-mercaptoethanol (0.0009 moles) as a 10% solution in water, 17.51 g (0.0591 moles) trimethylolpropane triacrylate, 86.08 g of methacrylic acid (1 mole), 48.05 g of methyl methacrylate (0.48 moles), and 49.14 g of ethyl acrylate (0.49 moles) is added subsurface to the reactor contents over a period of 100 minutes. The initiator solution described above continues to be fed simultaneously with no change in rate.

When the monomer mixture feed has finished, the initiator solution feed rate is doubled and is fed to completion, at which point the reactor temperature is increased to 90 C and the contents are cooked for one hour. The reactor contents are cooled to room temperature and 47 g of water are added to the white emulsion thus produced.

Examples 84-88 Personal Care Emulsion Formulations

Example 84

This example demonstrates the formulation of a moisturizing emulsion composition containing the alkali-swellable core-shell rheology modifier of Example 1. The formulation components are listed in Table 6.

TABLE 6

| Component | wt % |
|---|---|
| Water | q.s. to 100% |
| Polymer of Example 1 | 2 active wt % |
| 95% AMP-95 | 0.9 |
| Preservative | 1 |
| Oily phase: | |
| Hydrogenated isoparaffin | 7 |
| Cyclohexasiloxane | 6 |
| Isocetyl stearate | 7 |

The composition is formulated as follows:

The polymer emulsion of Example 1 is dissolved in water and then the preservative and 95% AMP-95 is added with stirring to form a clear solution. The oily phase is premixed and then added over 20 minutes into the aqueous phase with mixing. The final product is a stable emulsion.

Example 85

This example demonstrates the formulation of a moisturizing emulsion composition containing the alkali-swellable core-shell rheology modifier of Example 1. The formulation components are listed in Table 7.

TABLE 7

| Component | wt % |
|---|---|
| Water | q.s. to 100% |
| Polymer of Example 1 | 2 active wt % |
| Triethanolamine | 1.4 |
| Preservative | 1 |
| Oily phase: | |
| Hydrogenated isoparaffin | 12 |
| Cyclohexasiloxane | 8 |

The composition is formulated as follows:

The polymer emulsion of Example 1 is dispersed in water and then the triethanolamine and preservative is added with stirring, to form a clear solution. The oily phase is premixed and then added over 20 minutes into the aqueous phase with mixing. The final product is a stable emulsion.

Example 86

This example demonstrates the formulation of a moisturizing cream composition containing the alkali-swellable core-shell rheology modifier of Example 1. The formulation components are listed in Table 8.

TABLE 8

| Component | wt % |
|---|---|
| Phase A | |
| Polymer of Example 1 | 2 active wt % |
| 25% Sodium hydroxide | 1.5 |

TABLE 8-continued

| Component | wt % |
|---|---|
| Preservative | 0.15 |
| Water | q.s. to 100% |
| Phase B | |
| Cyclomethicone (cyclopentasiloxane) | 7 |
| Sweet almond oil | 8 |

The moisturizing cream is formulated as follows:

The polymer is added to the water with mixing and then sodium hydroxide is added, followed by the preservative. The emulsion is prepared by pouring the pre-mixed phase B into the phase A with stirring. Homogenization is subsequently carried out under pressure (500 bar).

A fluid emulsion is obtained which is particularly suitable as a moisturizing product.

Example 87

This example demonstrates the formulation of an emulsion containing the alkali-swellable core-shell rheology modifier of Example 1 suitable for aiding the removal of make-up. The formulation components are listed in Table 9.

TABLE 9

| Component | wt % |
|---|---|
| Phase A | |
| Polymer of Example 1 | 2 active wt % |
| 25% Sodium hydroxide | 1.5 |
| Preservative | 0.2 |
| Isoprene glycol | 5 |
| Demineralized water | q.s. to 100% |
| Phase B | |
| 2-Ethylhexyl palmitate | 20 |
| Liquid petrolatum | 7 |

The formulation procedure is identical to that of Example 86. An emulsion is obtained which is particular suitable for the removal of make-up from the skin.

Example 88

This example demonstrates the formulation of a night moisturizing cream for the face that contains the alkali-swellable core-shell rheology modifier of Example 1. The formulation components are listed in Table 10.

TABLE 10

| Component | wt % |
|---|---|
| Phase A | |
| Polymer of Example 1 | 2 active wt % |
| 25% Sodium hydroxide | 1.5 |
| Preservative | 0.1 |
| Glycerol | 7 |
| Demineralized water | q.s. to 100% |
| Phase B | |
| Liquid fraction of karite butter | 5 |
| Cyclomethicone (cyclopentasiloxane) | 7.5 |
| Hydrogenated isoparaffin | 5 |

The formulation procedure is identical to that of Example 86. An emulsion is obtained which is particularly suitable as a moisturizing product.

Examples 89-91—Pesticide Suspension Concentrates

The following examples demonstrate suspension concentrates of pesticides for use in agricultural applications formulated with polymers of the invention.

The solid pesticides (Tebuconazol available from Cambridge Chemical Technologies, MA; Azoxystrobin available from Syngenta, Basel Switzerland; Diuron available from Cambridge Chemical Technologies, MA) each were first wet-milled in a bead milling machine (Eiger Torrance Min-iMoto 250) to a particle size of ~5 micrometers. The compositions of the milled samples are shown in the weight percent indicated in Table 11.

TABLE 11

| Component | Milled sample MS-1 | Milled sample MS-2 | Milled sample MS-3 |
|---|---|---|---|
| Tebuconazole | 43 | | |
| Azoxystrobin | | | 45 |
| Diuron | | 43 | |
| Water | 50.53 | 56 | 46.99 |
| Propylene glycol | 5.38 | | 5 |
| Morwet EFW (available from AkzoNobel Surface Chemistry LLC) | 1.08 | 1 | |
| Isotridecyl alkoxylated phosphate ester, triethanolamine salt | | | 2.25 |
| Isotridecyl alcohol ethoxylate (IAE) | | | 0.75 |
| Agnique DFM 111 S (available from BASF) | 0.01 | | 0.01 |

The milled samples were used as the bases of the suspension concentrates. Examples 89 and 90 are suspension concentrates prepared by adding the core-shell polymers of Examples 1 and 29, respectively, to the milled samples MS-1 and MS-2 with stirring and adjusting the sample to a pH of about 6.3 with 12.5% caustic soda. Example 90 included additional water added to the milled sample. The amounts of each component are listed in Table 12.

TABLE 12

| Example | Milled sample | wt % milled sample | wt % water | Core-shell thickener | Wt % core-shell thickener | Wt % aq. NaOH (12.5% in water) | pH |
|---|---|---|---|---|---|---|---|
| 89 | MS-1 | 92.320 | 0 | Example 1 | 5.893 | 1.787 | 6.33 |
| 90 | MS-2 | 66.365 | 28.241 | Example 29 | 4.236 | 1.158 | 6.34 |

Upon two weeks storage at 50 C, neither Examples 88 nor 89 exhibited solid material sediment at the bottom of their containers, nor did they exhibit settling from the top surface of the suspension concentrate, as shown in Table 13.

TABLE 13

| Example | % Top clear | Sediment amount |
|---|---|---|
| 89 | No separation | No sediment |
| 90 | No separation | No sediment |

A third suspension concentrate was prepared by adding the core-shell polymer of Example 29 to the milled sample MS-3, and with continual stirring adding water, propylene glycol and a composition of 25 wt % phosphate ester (triethanolamine salt), and 75 wt % Isotridecyl alcohol ethoxylate (listed as "alc-EO-PO" in Table 14), and adjusting the sample to a pH of about 6.3 with caustic soda. The amounts of each component are listed in Table 14.

TABLE 14

| Example | Core-shell thickener | wt % of core-shell thickener | MS-3, wt % | Water, wt % | Propylene glycol, wt % | Phosphate ester:alc-EO-Po (75:25), wt % | NaOH (100%), wt % | pH |
|---|---|---|---|---|---|---|---|---|
| 91 | Example 29 | 1.997 | 31.456 | 60.852 | 3.495 | 2.097 | 0.102 | 6.93 |

The suspension concentrate of Example 90 was placed in a 50° C. oven for two weeks. Viscosity measured by Brookfield DV-I Prime with spindles 4 or 5 (contingent upon at 100, 50, 20, and 10 rpm was measured before and after storage, and sediment as well as settling of the solids from the top surface were monitored. The suspension concentrate viscosity was relatively stable over this period of time with little clearing from the top and no sediment. Data (including viscosity data reported in centipoise) are in Table 15 below.

TABLE 15

| Example | Viscosity before 50 C. treatment (Brookfield DV-I Prime spindle 4 or 5) | | | | After 2 weeks at 50 C. | | | | | |
|---|---|---|---|---|---|---|---|---|---|---|
| | 100 rpm | 50 rpm | 20 rpm | 10 rpm | 100 rpm | 50 rpm | 20 rpm | 10 rpm | % Top Clear | Sediment amount |
| 91 | 1340 | 2000 | 3340 | 5080 | 1324 | 1712 | 2360 | 3120 | 1% | None |

Example 92 (Back Acid Titration)

This example demonstrates the formulation of a shampoo composition that contains the polymer of Example 1.

200 grams of a shampoo base is prepared by adding 9 grams of the emulsion of Example 1 to 57.28 grams of deionized water in a 250 mL beaker. A small 1.5 inch jiffy mixer blade is inserted into the beaker and attached to an overhead mixer. The batch is allowed to mix with a vortex extending to the middle of the beaker. This is followed by adding 100 grams of sodium laureth sulfate (25.2% active Standapol ES-2 available from BASF) to the mixture, followed by another period of mixing for 15 minutes. Then, 2 grams of 25% sodium hydroxide is added and the mixture is agitated for 15 minutes. 14.8 grams of cocamidopropyl betaine (Crodateric CAB 20 available from Croda, Inc.) is added to the mixture and the mixture is agitated for another 15 minutes. Then 0.1 grams of (ethyleneditrilo)tetraacetic acid (tetrasodium salt) was added and the batch is mixed until homogeneous. 0.5 grams of sodium benzoate is added to the batch and mixed until homogeneous. The pH is then adjusted to pH 5.0+/−0.2 using 20% citric acid as needed. The product is a clear, viscous mixture suitable for use as a shampoo.

Example 93—Asphalt

This example demonstrates the formulation of an anionic, slow-setting asphalt emulsion for use in a tack coat application. The components and their weight percentages are listed in Table 16.

TABLE 16

| Component | Wt % |
|---|---|
| Water | q.s. to 100% |
| Polymer of Example 79 | 0.25 active wt % |
| 50% Sodium hydroxide | 0.13 |
| Redicote E-7000 (Available from AkzoNobel Surface Chemistry LLC) | 1.5 |
| Bitumen (40-90 pen) | 58 |

To prepare the anionic, slow-setting asphalt emulsion, the Redicote E-7000 and the polymer of Example 79 are dispersed in the water and the pH of the mixture is adjusted to pH 11 with 50% sodium hydroxide, and this mixture is heated to 50 C. The mixture is slowly mixed with hot (130 C) 40-90 penetration Bitumen by means of a laboratory colloid mill. The slow-setting emulsion produced is cooled to room temperature.

What is claimed is:

1. An alkali-swellable rheology modifier comprising a core-shell polymer, said core-shell polymer comprising a core polymer and a shell comprising at least one shell copolymer layer, wherein said core polymer and said at least one shell copolymer layer are each polymerized from a monomer mixture comprising a) one or more anionic ethylenically unsaturated monomers; and b) one or more hydrophobic ethylenically unsaturated monomers; the anionic ethylenically unsaturated monomer being present as greater than 10 mol % in the core polymer or at least one shell polymer layer; and the at least one shell copolymer layer being at least partially cross-linked and containing a mole percent of crosslinking monomer greater than the mole percent of crosslinking monomer in the core polymer, with the proviso that if the mole percent of crosslinking monomer in the core polymer is zero, then the core-shell polymer satisfies at least one of the following conditions:

(i) the core polymer is polymerized from a monomer mixture that comprises at least one associative monomer; or (ii) at least one shell copolymer layer is polymerized from monomer mixture that comprises at least one associative monomer.

2. The alkali-swellable rheology modifier of claim 1 wherein said core polymer and said at least one shell copolymer layer are each polymerized from a monomer mixture comprising a) one or more anionic ethylenically unsaturated monomers; b) one or more hydrophobic ethylenically unsaturated monomers; and further comprising one or more monomers selected from the group consisting of nonionic ethylenically unsaturated monomers; and one or more associative monomers.

3. The alkali swellable rheology modifier of claim 2 wherein said one or more nonionic ethylenically unsaturated monomers are selected from the group consisting of acrylamide, methacrylamide, N-$C_1$-$C_3$alkyl(meth)acrylamides, $C_1$-$C_3$dialkyl(meth)acrylamides, $C_1$ to $C_4$ hydroxyalkyl esters of (meth)acrylic acid, vinyl morpholine, vinyl pyrrolidone, vinyl propionate, vinyl butanoate, (poly) $C_1$-$C_4$alkoxylated (meth)acrylates, ethoxylated $C_1$-$C_4$alkyl, $C_1$-$C_4$alkaryl or aryl monomers, and combinations thereof.

4. The alkali swellable rheology modifier of claim 3 wherein at least one of said one or more nonionic ethylenically unsaturated monomers is selected from the group consisting of poly(ethylene glycol)$_n$ (meth)acrylate and poly (propylene glycol)$_n$ (meth)acrylate where n=1 to 100, methoxypolyethylene glycol (meth)acrylate, allyl glycidyl ether, allyl alcohol, and glycerol (meth)acrylate.

5. The alkali swellable rheology modifier of claim 1 wherein the core contains zero mole % crosslinking monomer, and the core is greater than 60 wt % of the core-shell polymer.

6. The alkali swellable rheology modifier of claim 1 wherein the core contains zero mole % crosslinking monomer, and the core comprises an associative monomer.

7. The alkali swellable rheology modifier of claim 1 wherein the core contains zero mole % crosslinking monomer, and at least one shell copolymer layer comprises an associative monomer.

8. The alkali swellable rheology modifier of claim 1 wherein the core contains zero mole % crosslinking monomer, and at least one shell copolymer layer comprises greater than 3 mole % crosslinking monomer, based on the moles of monomers in that shell copolymer layer not counting the crosslinking agent.

9. The alkali swellable rheology modifier of claim 1 wherein said core polymer comprises at least 0.01 mole % crosslinking monomer.

10. The alkali swellable rheology modifier of claim 1 wherein said one or more anionic ethylenically unsaturated monomers is selected from the group consisting of acrylic acid, methacrylic acid, 2-ethyl acrylic acid, α-chloro-acrylic acid, α-cyano acrylic acid, β-methyl-acrylic acid (crotonic acid), α-phenyl acrylic acid, β-acryloxy propionic acid, sorbic acid, α-chloro sorbic acid, angelic acid, 2-carboxyethyl (meth)acrylate, cinnamic acid, p-chloro cinnamic acid, β-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, muconic acid, 2-acryloxypropionic acid, 2-acrylamido-2-methyl propane sulfonic acid, vinyl sulfonic acid, sodium methallyl sulfonate, sulfonated styrene, allyloxybenzene sulfonic acid, and vinyl phosphonic acid, and combinations thereof.

11. The alkali swellable rheology modifier of claim 1 wherein said one or more hydrophobic ethylenically unsaturated monomers is selected from the group consisting of $C_1$-$C_{32}$ alkyl esters of acrylic and methacrylic acid; $C_4$-$C_{32}$ alkyl amides of acrylic and methacrylic acid; benzyl (meth)acrylate, phenyl (meth)acrylate, benzyl ethoxylate (meth)acrylate, phenyl ethoxylate (meth)acrylate, 6-hydroxyhexyl (meth)acrylate, and 10-hydroxydecyl (meth)acrylate, styrene, α-methyl styrene, vinyl toluene, t-butyl styrene, isopropyl styrene, and p-chlorostyrene; vinyl acetate, vinyl butyrate, vinyl caprolate, vinyl valerate, vinyl hexanoate, vinyl octanoate, vinyl nonanoate, vinyl decanoate, vinyl neodecanoate, vinyl laurate, vinyl caprolactam, (meth)acrylonitrile, isobutylene, isoprene, vinyl chloride, vinylidene chloride, 1-allyl naphthalene, 2-allyl naphthalene, 1-vinyl naphthalene, 2-vinyl naphthalene, and combinations thereof.

12. The alkali-swellable rheology modifier of claim 1 further comprising a spray-drying adjuvant.

13. The alkali-swellable rheology modifier of claim 1 which is in the form of an emulsion.

14. The alkali-swellable rheology modifier of claim 1 which is in the form of a dried powder.

15. An aqueous composition comprising the alkali-swellable rheology modifier of claim 1.

16. The aqueous composition of claim 15 wherein said composition is selected from the group consisting of personal care formulations, agricultural formulations, paint formulations, coating formulations, laundry and fabric care formulations, household cleaning formulations, industrial and institutional cleaning formulations, formulations for use in electronics industries, and formulations for use in construction industries.

17. A method of modifying the rheological properties of a formulation, comprising incorporating into said formulation the alkali-swellable rheology modifier of claim 1.

18. An alkali-swellable rheology modifier comprising a core-shell polymer, said core-shell polymer comprising a core polymer and a shell comprising at least one shell copolymer layer, wherein said core polymer and said at least one shell copolymer layer are each polymerized from a monomer mixture comprising a) one or more anionic ethylenically unsaturated monomers; and b) one or more hydrophobic ethylenically unsaturated monomers; the anionic ethylenically unsaturated monomer being present as greater than 10 mol % in the core polymer or at least one shell polymer layer; the core polymer containing at least 0.01 mole % crosslinking monomer; and the at least one shell copolymer layer being at least partially cross-linked and containing a mole percent of crosslinking monomer greater than the mole percent of crosslinking monomer in the core polymer.

* * * * *